US008945563B2

(12) United States Patent
Auf Der Maur et al.

(10) Patent No.: US 8,945,563 B2
(45) Date of Patent: Feb. 3, 2015

(54) METHOD FOR TREATING GLIOBLASTOMA USING ANTIBODIES BINDING TO THE EXTRACELLULAR DOMAIN OF THE RECEPTOR TYROSINE KINASE ALK

(75) Inventors: Adrian Auf Der Maur, Rütihof (CH); Alcide Barberis, Zürich (CH); Peter Lichtlen, Adliswil (CH)

(73) Assignee: Delenex Therapeutics AG, Schlieren (CH)

(*) Notice: Subject to any disclaimer, the term of this patent is extended or adjusted under 35 U.S.C. 154(b) by 1040 days.

(21) Appl. No.: 13/017,925

(22) Filed: Jan. 31, 2011

(65) Prior Publication Data

US 2011/0159008 A1 Jun. 30, 2011

Related U.S. Application Data

(62) Division of application No. 11/796,549, filed on Apr. 27, 2007, now Pat. No. 7,902,340.

(60) Provisional application No. 60/795,831, filed on Apr. 28, 2006.

(51) Int. Cl.
  *A61K 39/395* (2006.01)
  *C07K 16/28* (2006.01)
  *C07K 16/30* (2006.01)
  *A61K 39/00* (2006.01)

(52) U.S. Cl.
  CPC ............ *C07K 16/2896* (2013.01); *C07K 16/30* (2013.01); *A61K 2039/505* (2013.01); *C07K 2316/96* (2013.01); *C07K 2317/565* (2013.01); *C07K 2317/567* (2013.01); *C07K 2317/622* (2013.01); *C07K 2317/92* (2013.01); *C07K 2317/34* (2013.01)
  USPC ................................. 424/146.1; 424/141.1

(58) Field of Classification Search
  CPC . C12Q 1/6886; A61K 2300/00; A61K 38/00; G01N 33/57484
  See application file for complete search history.

(56) References Cited

U.S. PATENT DOCUMENTS

| 5,529,925 | A | 6/1996 | Morris et al. |
| 5,770,421 | A | 6/1998 | Morris et al. |
| 5,991,244 | A | 11/1999 | Kondo et al. |
| 6,174,674 | B1 | 1/2001 | Morris et al. |
| 6,451,997 | B1 | 9/2002 | Morris et al. |
| 6,696,548 | B2 | 2/2004 | Morris et al. |
| 7,528,109 | B2 | 5/2009 | Wellstein |
| 7,608,264 | B2 | 10/2009 | Wellstein |
| 2001/0021505 | A1 | 9/2001 | Morris et al. |
| 2002/0034768 | A1 | 3/2002 | Wellstein |
| 2009/0232815 | A1 | 9/2009 | Wellstein |
| 2010/0111964 | A1 | 5/2010 | Wellstein |

FOREIGN PATENT DOCUMENTS

| EP | 1479694 A2 | 11/2004 |
| WO | 95/15331 A1 | 6/1995 |
| WO | 01/96394 A2 | 12/2001 |
| WO | 03/097697 A2 | 11/2003 |
| WO | 2006/020684 A2 | 2/2006 |

OTHER PUBLICATIONS

Lamminmäki U, et al. Crystal structure of a recombinant anti-estradiol Fab fragment in complex with 17beta-estradiol. The Journal of biological chemistry, vol. 276(39):36687-36694 (2001).
Klimka, A. et al., "Human anti-CD30 recombinant antibodies by guided phage antibody selection using cell panning," British Journal of Cancer, vol. 83(2):252-260 (2000).
Beiboer, Sigrid, et al., "Guided selection of a pan carcinoma specific antibody reveals similar binding characteristics yet structural divergence between the original murine antibody and its human equivalent" Journal of Molecular Biology, vol. 296:833-849, (2000).
Barbas, S.M, et al. "Human autoantibody recognition of DNA" Proceeding of the National Academy of Sciences, vol. 92 (7):2529-2533 (1995).
Lederman, Seth, et al. "A single amino acid substitution in a common African allele of the CD4 molecule ablates binding of the monoclonal antibody, OKT4" Molecular Immunology, vol. 28:1171-1181 (1991).
Li, C.H., et al. "Beta-Endorphin omission analogs: dissociation of immunoreactivity from other biological activities" Proceeding of the National Academy of Sciences, vol. 77:3211-3214 (1980).
Houghten, et al. "New Approaches to Immunization, Vaccines 86" Cold Spring Harbor Laboratory, p. 21-25 (1986).
Bernard-Pierrot, Isabelle, et al., "Dominant Negative Effectors of Heparin Affin Regulatory Peptide (HARP) Angiogenic and Transforming Activities" The Journal of Biological Chemistry, vol. 277:32071-32077 (2002).
Auf der Maur, Adrian et al., "Antigen-independent selection of stable intracellular single-chain antibodies," FEBS Letters, vol. 508:407-412 (2001).
Auf der Maur, Adrian et al., "Antigen-independent selection of intracellular stable antibody frameworks," Methods, vol. 34:215-224 (2004).
Auf der Maur, Adrian et al., "Direct in Vivo Screening of Intrabody Libraries Constructed on a Highly Stable Single-chain Framework," The Journal of Biological Chemistry, vol. 277(47):45075-45085 (2002).
Bai, Ren-Yuan et al., "Nucleophosmin-anaplastic lymphoma kinase associated with anaplastic large-cell lymphoma activates the phosphatidylinositol 3-kinase/Akt antiapoptotic signaling pathway," Blood, vol. 96(13):4319-4327 (2000).
Barbas, Shana M. et al., "Recognition of DNA by Synthetic Antibodies," J. Am. Chem. Soc., vol. 116:2161-2162 (1994).
Bowden, Emma T. et al., "Anti-apoptotic Signaling of Pleiotrophin through Its Receptor, Anaplastic Lymphoma Kinase," The Journal of Biological Chemistry, vol. 277(39):35862-35868 (2002).
Chothia, Cyrus et al., "Canonical Structures for the Hypervariable Regions of Immunoglobulins," J. Mol. Biol., vol. 196:901-917 (1987).

(Continued)

*Primary Examiner* — Sharon Wen
(74) *Attorney, Agent, or Firm* — Lathrop & Gage LLP; James H. Velema, Esq.; Andrew T. Wilkins, Esq.

(57) ABSTRACT

The present invention concerns an antibody specific for human ALK (Anaplastic Lymphoma Kinase), in particular a scFv, a nucleic acid sequence encoding it, its production and its use as a pharmaceutical or for diagnostic purposes. Said antibody is suitable for the local treatment of tumors, in particular glioblastoma.

16 Claims, 5 Drawing Sheets

(56) References Cited

OTHER PUBLICATIONS

Chothia, Cyrus et al., "Domain Association in Immunoglobulin Molecues. The Packing of Variable Domains," J. Mol. Biol., vol. 186:651-663 (1985).
Choudhuri, Rangana et al., "An Angiogenic Role for the Neurokines Midkine and Pleiotrophin in Tumorigenesis," Cancer Research, vol. 57:1814-1819 (1997).
Clackson, Tim et al., "Making antibody fragments using phage display libraries," Nature, vol. 352:624-628 (1991).
Czubayko, Frank et al., "Melanoma angiogenesis and metastasis modulated by ribozyme targeting of the secreted growth factor pleiotrophin," Proc. Natl. Acad. Sci. USA, vol. 93:14753-14758 (1996).
De Juan, Carmen et al., "Genomic organization of a novel glycosylphosphatidylinositol MAM gene expressed in human tissues and tumors," Oncogene, vol. 21:3089-3094 (2002).
Delsol, Georges et al., "A New Subtype of Large B-Cell Lymphoma Expressing the ALK Kinase and Lacking the 2;5 Translocation," Blood, vol. 89(5):1483-1490 (1997).
Dirks, Willy G. et al., "Expression and Functional Analysis of the Anaplastic Lymphoma Kinase (ALK) Gene in Tumor Cell Lines," Int. J. Cancer, vol. 100:49-56 (2002).
Ditzel, Henrik J. et al., "Determinants of Polyreactivity in a Large Panel of Recombinant Human Antibodies from HIV-1 Infection," The Journal of Immunology, vol. 157:739-749 (1996).
Duyster, Justus et al., "Translocations involving anaplastic lymphoma kinase (ALK)," Oncogene, vol. 20:5623-5637 (2001).
Ergin, Melek et al., "Inhibition of tyrosine kinase activity induces caspase-dependent apoptosis in anaplastic large cell lymphoma with NPM-ALK (p80) fusion protein," Experimental Hematology, vol. 29:1082-1090 (2001).
Fang, Wenjing et al., "Pleiotrophin Stimulates Fibroblasts and Endothelial and Epithelial Cells and Is Expressed in Human Cancer," The Journal of Biological Chemistry, vol. 267(36):25889-25897 (1992).
Fiorani, C. et al., "Primary systemic anaplastic large-cell lymphoma (CD30+): advances in biology and current therapeutic approaches," Clinical Lymphoma, vol. 2(1):29-37 (2001).
Iwahara, Toshinori et al., "Molecular characterization of ALK, a receptor tyrosine kinase expressed specifically in the nervous system," Oncogene, vol. 14:439-449 (1997).
Kutok, Jeffery L. et al., "Molecular Biology of Anaplastic Lymphoma Kinase-Positive Anaplastic Large-Cell Lymphoma," Journal of Clinical Oncology, vol. 20(17):3691-3702 (2002).
Ladanyi, Marc et al., "Aberrant ALK Tyrosine Kinase Signaling. Different Cellular Lineages, Common Oncogenic Mechanisms?" American Journal of Pathology, vol. 157(2):341-345 (2000).
Lamant, Laurence et al., "Expression of the ALK Tyrosine Kinase Gene in Neuroblastoma," American Journal of Pathology, vol. 156(5):1711-1721 (2000).
Li, Xiao-Qiu et al., "Expression of Anaplastic Lymphoma Kinase in Soft Tissue Tumors: An Immunohistochemical and Molecular Study of 249 Cases," Human Pathology, vol. 35(6):711-721 (2004).
Loren, Christina E. et al., "Identification and characterization of DAlk: a novel *Drosophila melanogaster* RTK which drives ERK activation in vivo," Genes Cells, vol. 6(6):531-544 (2001).
Miyake, Izumi et al., "Activation of anaplastic lymphoma kinase is responsible for hyperphosphorylation of ShcC in neuroblastoma cell lines," Oncogene, vol. 21:5823-5834 (2002).
Morris, Stephan W. et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, vol. 14:2175-2188 (1997).
Morris, Stephan W. et al., "ALK+ CD30+ Lymphomas: A Distinct Molecular Genetic Subtype of non-Hodgkin's Lymphoma," British Journal of Hematology, vol. 113:275-295 (2001).
O'Brien, Tim et al., "The Angiogenic Factor Midkine Is Expressed in Bladder Cancer, and Overexpression Correlates with a Poor Outcome in Patients with Invasive Cancers," Cancer Research, vol. 56:2515-2518 (1996).

Padlan, Eduardo A. et al., "Anatomy of the Antibody Molecule," Molecular Immunology, vol. 31(3):169-217 (1994).
Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Powers, Ciaran et al., "Pleiotrophin Signaling through Anaplastic Lymphoma Kinase Is Rate-limiting for Glioblastoma Growth," The Journal of Biological Chemistry, vol. 277(16):14153-14158 (2002).
Pulford, Karen et al., "Anaplastic lymphoma kinase proteins and malignancy," Current Opinion in Hematology, vol. 81:231-236 (2001).
Pulford, K. et al., "Anaplastic Lymphoma Kinase Proteins in Growth Control and Cancer," Journal of Cellular Physiology, vol. 199:330-358 (2004).
Rader, Christoph et al., "A phage display approach for rapid antibody humanization: Designed combinatorial V gene libraries," Proc. Natl. Acad. Sci. USA, vol. 95:8910-8915 (1998).
Schaerer-Brodbeck, Claudia et al., "Coupling homologous recombination with growth selection in yeast: a tool for construction of random DNA sequence libraries," BioTechniques, vol. 37(2):202-206 (2004).
Stoica, Gerald E. et al., "Midkine Binds to Anaplastic Lymphoma Kinase (ALK) and Acts as a Growth Factor for Different Cell Types," The Journal of Biological Chemistry, vol. 277(39):35990-35998 (2002).
Weber, Dirk et al., "Pleiotrophin Can Be Rate-limiting for Pancreatic Cancer Cell Growth," Cancer Research, vol. 60:5284-5288 (2000).
Wellstein, Anton et al., "A Heparin-binding Growth Factor Secreted from Breast Cancer Cells Homologous to a Developmentally Regulated Cytokine," The Journal of Biological Chemistry, vol. 267(4):2582-2587 (1992).
International Search Report for Application No. PCT/CH2007/000202, dated Oct. 19, 2007.
International Preliminary Report on Patentability for Application No. PCT/CH2007/000202, dated Oct. 28, 2008.
Rudikoff et al.; Single amino acid substitution altering antigen-binding specificity; Proc Natl Acad Sci USA 1982 vol. 79 p. 1979.
MacCallum et al. Antibody-antigen interactions: contact analysis and binding site topography; J. Mol. Biol. (1996) 262, 732-745.
Pascalis et al.; Grafting of "abbreviated" complementarity-determining regions containing specificity-determining residues essential for ligand contact to engineer a less immunogenic humanized monoclonal antibody; The Journal of Immunology (2002) 169, pp. 3076-3084.
Casset et al.; A peptide mimetic of an anti-CD4 monoclonal antibody by rational design; BBRC 2003, 307:198-205.
Vajdos et al. Comprehensive functional maps of the antigen-binding site of an anti-ErbB2 antibody obtained with shotgun scanning mutagenesis; J. Mol. Biol. (2002) 320, 415-428.
Chen et al.; Selection and analysis of an optimized anti-VEGF antibody: crystal structure of an affinity-matured fab in complex with antigen; J. Mol. Bio. (1999) 293, 865-881.
Wu et al.; Humanization of a murine monoclonal antibody by simultaneous optimization of framework and CDR residues; J. Mol. Biol. (1999) 294, 151-162.
Padlan et al.; Structure of an antibody-antigen complex: crystal structure of the HyHEL-10 Fab-lysozyme complex; PNAS 1989, 86:5938-5942.
Lamminmaki et al.; Crystal Structure of a Recombinant Anti-estradiol Fab Fragment in Complex with 17β-Estradiol; JBC 2001, 276:36687-36694.
Auf der Maur, Adrian, et al. "Antigen-independent selection of stable intracellular single-chain antibodies," FEBS Letters vol. 508:407-412 (2001).
Auf der Maur, Adrian, et al. "Antigen-independent selection of intracellular stable antibody frameworks" Methods, vol. 34:215-224 (2004).
Auf der Maur, Adrian, et al., "Direct in vivo screening of intrabody libraries constructed on a highly stable single-chain framework" Journal of Biological Chemistry, vol. 277(47): 45075-85 (2002).
Bai, Ren-Yuan, et al. "Nucleophosmin-anaplastic lymphoma kinase associated with anaplastic large-cell lymphoma activates the

(56) References Cited

OTHER PUBLICATIONS phosphatidylinositol 3-kinase/Akt anti-apoptotic signalling pathway" Blood, vol. 96(13):4319-4327 (2000).
Bowden Emma T. et al. "Anti-apoptotic signaling of pleiotrophin through its receptor, anaplastic lymphoma kinase" The Journal of Biological Chemistry vol. 277(39):35862-35868 (2002).
Chothia, Cyrus, et al. "Canonical structures for the hypervariable regions of immunoglobulins" J. Mol. Biol., vol. 196:901-917 (1987).
Chothia, Cyrus, et al. "Domain association in immunoglobulin molecules. The packing of variable domains" J. Mol. Biol., vol. 186:651-663 (1985).
Choudhuri, Rangana, et al., "An Angiogenic Role for the Neurokines Midkine and Pleiotrophin in Tumorigenesis" Cancer Research, vol. 57:1814-1819 (1997).
Czubayko, Frank et al., "Melanoma angiogenesis and metastasis modulated by ribozyme targeting of the secreted growth factor pleiotrophin" Proc. Natl. Acad. Sci. USA, vol. 93:14753-14758 (1996).
De Juan, Carmen, et al., "Genomic organization of a novel glycosylphosphatidylinositol MAM gene expressed in human tissues and tumors" Oncogene, vol. 21:3089-3094 (2002).
Delsol Georges, et al., "A new subtype of large B-cell lymphoma expressing the ALK kinase and lacking the 2; 5 translocation" Blood, vol. 89(5):1483-1490 (1997).
Dirks, Willy G., et al., "Expression and functional analysis of the anaplastic lymphoma kinase (ALK) gene in tumor cell lines" International Journal of Cancer, vol. 100:49-56 (2002).
Ditzel, Henrik J., et al., "Determinants of Polyreactivity in a Large Panel of Recombinant Human Antibodies from HIV-1 Infection" The Journal of Immunology, vol. 157:739-749 (1996).
Duyster Justus et al., "Translocations involving anaplastic lymphoma kinase (ALK)" Oncogene, vol. 20:5623-5637 (2001).
Ergin Melek, et al., "Inhibition of tyrosine kinase activity induces caspase-dependent apoptosis in anaplastic large cell lymphoma with NPM-ALK (p80) fusion protein" Experimental Hematology, vol. 29:1082-1090 (2001).
Fang, Wenjing, et al., "Pleiotrophin stimulates fibroblasts and endothelial and epithelial cells and is expressed in human cancer" The Journal of Biological Chemistry, vol. 267(36):25889-25897 (1992).
Fiorani, C. et al., "Primary systemic anaplastic large-cell lymphoma (CD30+): advances in biology and current therapeutic approaches" Clinical Lymphoma, vol. 2(1):29-37 (2001).
Iwahara, Toshinori, et al, "Molecular characterization of ALK, a receptor tyrosine kinase expressed specifically in the nervous system" Oncogene, vol. 14:439-449 (1997).
Kutok, Jeffrey L., et al. "Molecular biology of anaplastic lymphoma kinase-positive anaplastic large-cell lymphoma" Journal of Clinical Oncology, vol. 20(17):3691-3702 (2002).
Ladanyi Marc, et al., "Aberrant ALK tyrosine kinase signalling. Different cellular lineages, common oncogenic mechanisms?" American Journal of Pathology, vol. 157(2):341-345 (2000).
Lamant, Laurence et al., "Expression of the ALK tyrosine kinase gene in neuroblastoma" American Journal of Pathology, vol. 156:1711-1721 (2000).
Li, Xiao-Qiu, et al., "Expression of Anaplastic Lymphoma Kinase in soft tissue tumors: an immunohistochemical and molecular study of 249 cases" Human Pathology, vol. 35:711-721 (2004).
Loren Christina E. et al., "Identification and characterization of Dalk: a novel *Drosophila melanogaster* RTK which drives ERK activation in vivo" Genes to Cells, vol. 6(6):531-544 (2001).
Miyake Izumi, et al., "Activation of anaplastic lymphoma kinase is responsible for hyperphosphorylation of ShcC in neuroblastoma cell lines" Oncogene, vol. 21:5823-5834 (2002).
Morris, Stephan W., et al., "ALK, the chromosome 2 gene locus altered by the t(2; 5) in non-Hodgkin's lymphoma, encodes a novel neural receptor tyrosine kinase that is highly related to leukocyte tyrosine kinase (LTK)" Oncogene, vol. 14:2175-2188 (1997).

Morris Stephan W., et al., "ALK+CD30+ lymphomas: A distinct molecular genetic subtype of non-Hodgkin's lymphoma" British Journal of Haematology, vol. 113:275-295 (2001).
O'Brien, Tim, et al., "The angiogenic factor midkine is expressed in bladder cancer and overexpression correlates with a poor outcome in patients with invasive cancer" Cancer Research, vol. 56:2515-2518 (1996).
Padlan, Eduardo A, et al, "Anatomy of the antibody molecule" Molecular Immunology, vol. 31:169-217 (1994).
Portolano, Stefano, et al., "Lack of Promiscuity in Autoantigen-Specific H and L Chain Combination as Revealed by Human H and L Chain 'Roulette'" The Journal of Immunology, vol. 150(3):880-887 (1993).
Powers Ciaran, et al., "Pleiotrophin signalling through anaplastic lymphoma kinase is rate-limiting for glioblastoma growth" The Journal of Biological Chemistry, vol. 277(16):14153-14158 (2002).
Pulford Karen, et al., "Anaplastic lymphoma kinase proteins and malignancy" Current Opinion in Hematology, vol. 81:231-236 (2001).
Pulford K. et al., "Anaplastic lymphoma kinase proteins in growth control and cancer" Journal of Cellular Physiology, vol. 199:330-358 (2004).
Rader, Christoph, et al. "A phage display approach for rapid antibody humanization: Designed combinatorial V gene libraries" Proc. Natl. Acad. Sci. USA, vol. 95:8910-8915 (1998).
Schaerer-Brodbeck, Claudia, et al., "Coupling homologous recombination with growth selection in yeast: a tool for construction of random DNA sequence libraries" Biotechniques, vol. 37(2):202-206 (2004).
Stoica, Gerald E. et al., "Midkine binds to anaplastic lymphoma kinase (ALK) and acts as a growth factor for different cell types" The Journal of Biological Chemistry, vol. 277 (39):35990-35998 (2002).
Weber Dirk. et al., "Pleiotrophin can be rate-limiting for pancreatic cancer cell growth" Cancer Research, vol. 60:5284-5288 (2000).
Wellstein, Aton et al., "A Heparin-binding Growth Factor Secreted from Breast Cancer Cells Homologous to a Developmentally Regulated Cytokine" The Journal of Biological Chemistry, vol. 267:2582-2587 (1992).
Rudikoff, Stuart, et al. "Single amino acid substitution altering antigen-binding specificity" Proc. Ntl. Acad. Sci. USA, vol. 79:1979-1983, (1982).
MacCallum, Robert M., et al., "Antibody-antigen Interactions: Contact Analysis and Binding Site Topography" Journal of Molecular Biology, vol. 262:732-745 (1996).
Pascalis, Roberto De, et al. Grafting of 'Abbreviated' Complementarity-Determining Regions Containing Specificity-Determining Residues Essential for Ligand Contact to Engineer a Less Immunogenic Humanized Monoclonal Antibody, Journal of Immunology, vol. 169:3076-3084 (2002).
Casset et al. BBRC, vol. 307:198-205 (2003).
Chen, Yvonne et al., "Selection and analysis of an optimized anti-VEGF antibody: crystal structure of an affinity-matured fab in complex with antigen" Journal of Molecular Biology, vol. 293:865-881 (1999).
Vajdos, Adams, et al. "Comprehensive functional maps of the antigen binding site of an anti-ErbB2 antibody obtained by shotgun scanning mutagenesis" Journal of Molecular Biology, vol. 320:415-428 (2002).
Wu, et al., "Humanization of a murine monoclonal antibody by simultaneous optimization of framework and CDR residues" Journal of Molecular Biology, vol. 294:151-162 (1999).
Stoica, Gerald E. et al., "Identification of anaplastic lymphoma kinase as a receptor for the growth factor pleiotrophin" The Journal of Biological Chemistry, vol. 276(20):16772-16779 (2001).
Padian, E., et al, "Structure of an antibody-antigen complex: Crystal structure of the HyHEL-1 0 Fab-lysozyme complex", Proc. Natl. Acad. Sci USA 86:5938-5942 (1989).
Klimka, et al., Human anti-CD30 recombinant antibodies by duided phage antibody selection using cell panning, British Journal of Cancer, 2000, 83:pp. 252-26.
Beiboer, et al.; Guided selection of a pan carcinoma specific antibody reveals similar binding characteristics yet structural divergence

(56) References Cited

OTHER PUBLICATIONS between the original murine antibody and its human equivalent; J Mol Biol. Feb. 25, 2000;296(3):833-49.

Barbas et al.; Human autoantibody recognition of DNA; PNAS 1995, 92:2529-2533.

Lederman et al.; A single amino acid substitution in a common african allele of the CD4 molecule ablates binding of the monoclonal antibody, OKT4; Molecular Immunology 28: 1171-1181, 1991.

Li et al.; beta-Endorphin omission analogs: dissociation of immunoreactivity from other biological activities; PNAS 77: 3211-3214, 1980.

Houghten et al.; New Approaches to Immunization; Vaccines 86, Cold Spring Harbor Laboratory, p. 21-25, 1986.

Bernard-Pierrot et al.; Protein Structure and Folding: Dominant Negative Effectors of Heparin Affin Regulatory Peptide (HARP) Angiogenic and Transforming Activities; JBC 2002, 277:32071-32077.

Stoica et al.; Identification of anaplastic lymphoma kinase as a receptor for the growth factor pleiotrophin; JBC 2001, 276:16772-16779.

ELISA: GST-ALK peptide
$K_d$
1° binder: 31.0 ± 1.3 nM
2° binder:  7.2 ± 1.4 nM → ESBA521

Human ALK

ESBA521               polyclonal AB

SEQUENCE LISTING

<160> NUMBER OF SEQ ID NOS: 100

<210> SEQ ID NO 1
<211> LENGTH: 16
<212> TYPE: PRT
<213> ORGANISM: Homo sapiens

<400> SEQUENCE: 1

Gly Arg Ile Gly Arg Pro Asp Asn Pro Phe Arg Val Ala Leu Glu Tyr
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide: CDR3 of the heavy chain
      variable region of ESBA512

<400> SEQUENCE: 2

Arg Asp Ala Trp Leu Asp Val Leu Ser Asp Gly Phe Asp Tyr
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of ESBA512

<400> SEQUENCE: 3

Ala Thr Trp Asp Asn Asp Lys Trp Gly Val Val
1               5                   10

<210> SEQ ID NO 4
<211> LENGTH: 122
<212> TYPE: PRT
<213> ORGANISM: Artificial Sequence
<220> FEATURE:
<223> OTHER INFORMATION: Synthetic peptide: Heavy chain variable region
      of ESBA512

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Trp Leu Asp Val Leu Ser Asp Gly Phe Asp Tyr Trp
            100                 105                 110

Gly Gln Gly Thr Leu Val Thr Val Ser Ser
        115                 120

<210> SEQ ID NO 5
<211> LENGTH: 111

-continued

```
<212> TYPE: PRT
<213> ORGANISM: Artificial Sequence
<220> FEATURE:
<223> OTHER INFORMATION: Synthetic peptide: Light chain variable region
      of ESBA512

<400> SEQUENCE: 5

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Asn Asp Lys
                85                  90                  95

Trp Gly Val Val Phe Gly Gly Gly Thr Lys Leu Glu Val Leu Gly
            100                 105                 110

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of ESBA512

<400> SEQUENCE: 6

Ala Ile Ser Gly Ser Gly Gly Ser Thr Tyr Tyr Ala Asp Ser Val Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 265.1

<400> SEQUENCE: 7

Ala Ile Asn Met Lys Gly Asn Asp Arg Tyr Tyr Ala Asp Ser Val Gly
1               5                   10                  15

Lys

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide: CDR2 of the heavy chain
      variable region of the scFv 43.2

<400> SEQUENCE: 8

Ala Ile Arg Thr Asn Ser Lys Glu Tyr Tyr Ala Asp Ser Val Lys Gly
1               5                   10                  15

<210> SEQ ID NO 9
<211> LENGTH: 17
<212> TYPE: PRT
```

```
<213> ORGANISM: Artificial Sequence
<220> FEATURE:
<223> OTHER INFORMATION: Synthetic peptide: CDR2 of the heavy chain
      variable region of the scFv 100.2

<400> SEQUENCE: 9

Ala Ile Lys Thr Asp Gly Asn His Lys Tyr Tyr Ala Asp Ser Val Lys
1               5                   10                  15

Gly

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide: CDR2 of the heavy chain
      variable region of scFv 2.11

<400> SEQUENCE: 10

Arg Thr Asp Ser Lys Glu Gln Tyr Tyr Ala Asp Ser Val Lys Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide: CDR2 of the heavy chain
      variable region of the scFv 28.11

<400> SEQUENCE: 11

Glu Thr Ser Ser Gly Ser Thr Tyr Tyr Ala Asp Ser Val Lys Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide: CDR2 of the heavy chain
      variable region of the scFv 33.11

<400> SEQUENCE: 12

Asn Thr Gly Gly Gly Ser Thr Tyr Tyr Ala Asp Ser Val Lys Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide: CDR2 of the heavy chain
      variable region of the scFv 4.12

<400> SEQUENCE: 13

Asn Thr Arg Gly Gln Asn Glu Tyr Tyr Ala Asp Ser Val Lys Gly
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of framework 4.4

<400> SEQUENCE: 14
```

```
Gly Thr Trp Asp Ser Ser Leu Ser Gly Val Val
1               5                   10
```

<210> SEQ ID NO 15
<211> LENGTH: 248
<212> TYPE: PRT
<213> ORGANISM: Artificial Sequence
<220> FEATURE:
<223> OTHER INFORMATION: Synthetic peptide: sequence of framework 5.2

<400> SEQUENCE: 15

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Leu Thr His Tyr
                20                  25                  30

Leu Ala Trp Tyr Gln Gln Lys Pro Gly Gln Ala Pro Arg Leu Leu Ile
            35                  40                  45

Tyr Asp Thr Ser Lys Arg Ala Thr Gly Thr Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Ser Ala Leu Tyr Tyr Cys Gln Gln Arg Asn Ser Trp Pro His
                85                  90                  95

Thr Phe Gly Gly Gly Thr Lys Leu Glu Ile Lys Arg Gly Gly Gly Gly
            100                 105                 110

Gly Ser Gly Gly Gly Gly Ser Gly Gly Gly Gly Ser Ser Gly Gly Gly
        115                 120                 125

Ser Glu Val Gln Leu Val Glu Ser Gly Gly Gly Val Ala Gln Pro Gly
    130                 135                 140

Gly Ser Leu Arg Val Ser Cys Ala Ala Ser Gly Phe Ser Phe Ser Ser
145                 150                 155                 160

Tyr Ala Met Gln Trp Val Arg Gln Ala Pro Gly Lys Gly Leu Glu Trp
                165                 170                 175

Val Ala Val Ile Ser Asn Asp Gly Arg Ile Glu His Tyr Ala Asp Ala
            180                 185                 190

Val Arg Gly Arg Phe Thr Ile Ser Arg Asp Asn Ser Gln Asn Thr Val
        195                 200                 205

Phe Leu Gln Met Asn Ser Leu Arg Ser Asp Asp Thr Ala Leu Tyr Tyr
    210                 215                 220

Cys Ala Arg Glu Ile Gly Ala Thr Gly Tyr Leu Asp Asn Trp Gly Gln
225                 230                 235                 240

Gly Thr Leu Val Thr Val Ser Ser
                245
```

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide: Linker connecting VH and VL
      in ESBA512

<400> SEQUENCE: 16

```
Gly Gly Gly Gly Ser Gly Gly Gly Ser Gly Gly Gly Gly Ser Ser
1               5                   10                  15

Gly Gly Gly Ser
            20
```

```
<210> SEQ ID NO 17
<211> LENGTH: 8
<212> TYPE: PRT
<213> ORGANISM: Artificial Sequence
<220> FEATURE:
<223> OTHER INFORMATION: Synthetic peptide: C-terminal half of CDR2 of
      ESBA521 and its derivatives.

<400> SEQUENCE: 17

Tyr Tyr Ala Asp Ser Val Lys Gly
1               5

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide: CDR3 of the heavy chain
      variable sequence of framework 4.4

<400> SEQUENCE: 18

Asp Ala Gly Ile Ala Val Ala Gly Thr Gly Phe Asp Tyr
1               5                   10

<210> SEQ ID NO 19
<211> LENGTH: 253
<212> TYPE: PRT
<213> ORGANISM: Artificial Sequence
<220> FEATURE:
<223> OTHER INFORMATION: Synthetic peptide: Single chain antibody
      fragment ESBA512

<400> SEQUENCE: 19

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Asn Asp Lys
                85                  90                  95

Trp Gly Val Val Phe Gly Gly Gly Thr Lys Leu Glu Val Leu Gly Gly
            100                 105                 110

Gly Gly Ser Gly Gly Gly Gly Ser Gly Gly Gly Ser Ser Gly
            115                 120                 125

Gly Gly Ser Glu Val Gln Leu Val Glu Ser Gly Gly Leu Val Gln
    130                 135                 140

Pro Gly Gly Ser Leu Arg Leu Ser Cys Ala Ala Ser Gly Phe Thr Phe
145                 150                 155                 160

Ser Ser Tyr Ala Met Ser Trp Val Arg Gln Ala Pro Gly Lys Gly Leu
                165                 170                 175

Glu Trp Val Ser Ala Ile Ser Gly Ser Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220
```

```
Tyr Tyr Cys Ala Arg Asp Ala Trp Leu Asp Val Leu Ser Asp Gly Phe
225                 230                 235                 240

Asp Tyr Trp Gly Gln Gly Thr Leu Val Thr Val Ser Ser
                245                 250

<210> SEQ ID NO 20
<211> LENGTH: 253
<212> TYPE: PRT
<213> ORGANISM: Artificial Sequence
<220> FEATURE:
<223> OTHER INFORMATION: Synthetic peptide: scFv serving as framework

<400> SEQUENCE: 20

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Leu Pro Gly Thr Ala Pro Gln Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Gly
            100                 105                 110

Gly Gly Ser Gly Gly Gly Gly Ser Gly Gly Gly Gly Ser Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Ser Ser Tyr Ala Met Ser Trp Val Arg Gln Ala Pro Gly Lys Gly Leu
                165                 170                 175

Glu Trp Val Ser Ala Ile Ser Gly Ser Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Ala Gly Ile Ala Val Ala Gly Thr Gly Phe
225                 230                 235                 240

Asp Tyr Trp Gly Gln Gly Thr Leu Val Thr Val Ser Ser
                245                 250

<210> SEQ ID NO 21
<211> LENGTH: 333
<212> TYPE: DNA
<213> ORGANISM: Artificial Sequence
<220> FEATURE:
<223> OTHER INFORMATION: Synthetic polynucleotide: Light chain variable
      region of ESBA512

<400> SEQUENCE: 21
cagtctgtgc tgacgcagcc gccctcagtg tctgcggccc caggacagaa ggtcaccatc      60
tcctgctccg gaagcaccct caacattggc gataattatg tatcctggta ccaacaactc     120
```

```
ccaggaacag ccccccaact cctcatttat gacaatacta aacgaccctc agggattcct      180
gaccggttct ctggctccaa gtctggcacg tcagccaccc tgggcatcac cggactccag      240
actggggacg aggccgatta ttactgcgcg acctgggata tgataagtg gggtgtggtt       300 ttcggcggag ggaccaagct cgaggtccta ggt                                   333

<210> SEQ ID NO 22
<211> LENGTH: 366
<212> TYPE: DNA
<213> ORGANISM: Artificial Sequence
<220> FEATURE:
<223> OTHER INFORMATION: Synthetic polynucleotide: Variable region of
      the heavy chain of ESBA512

<400> SEQUENCE: 22
gaggtgcagc tggtggagtc cggggggaggc ttggtacagc ctggggggtc cctgagactc     60
tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat    240
ctgcaaatga acagcctgag agccgaggac acggccgtat attactgcgc gcgtgatgcg   300
tggttggatg tgctttcgga tggctttgac tactggggcc agggaaccct ggtcaccgtc  360
tcctcg                                                              366

<210> SEQ ID NO 23
<211> LENGTH: 759
<212> TYPE: DNA
<213> ORGANISM: Artificial Sequence
<220> FEATURE:
<223> OTHER INFORMATION: Synthetic polynucleotide: single chain antibody

<400> SEQUENCE: 23
cagtctgtgc tgacgcagcc gccctcagtg tctgcggccc caggacagaa ggtcaccatc    60
tcctgctccg gaagcaccts caacattggc gataattatg tatcctggta ccaacaactc   120
ccaggaacag ccccccaact cctcatttat gacaatacta aacgaccctc agggattcct   180
gaccggttct ctggctccaa gtctggcacg tcagccaccc tgggcatcac cggactccag   240
actggggacg aggccgatta ttactgcgcg acctgggata tgataagtg gggtgtggtt    300 ttcggcggag ggaccaagct cgaggtccta ggtggtggtg gtggttctgg tggtggtggt  360 tctgcggcg cgggctccag tggtggtgga tccgaggtgc agctggtgga gtccggggga  420
ggcttggtac agcctggggg gtccctgaga ctctcctgtg cagcctctgg attcaccttt  480
agcagctatg ccatgagctg gtccgccag gctccaggga aggggctgga gtgggtctca   540
gctattagtg gtagtggtgg tagcacatac tacgcagact ccgtgaaggg ccggttcacc   600
atctccagag acaattccaa gaacacgctg tatctgcaaa tgaacagcct gagagccgag   660
gacacggccg tatattactg cgcgcgtgat gcgtggttgg atgtgctttc ggatggcttt   720
gactactggg gccagggaac cctggtcacc gtctcctcg                          759

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide: CDR3 of the variable region
      of the heavy chain of framework 4.4
```

<400> SEQUENCE: 24

Asp Ala Gly Ile Ala Val Ala Gly Thr Gly Phe Asp Tyr
1 5 10

<210> SEQ ID NO 25
<211> LENGTH: 13
<212> TYPE: PRT
<213> ORGANISM: Artificial Sequence
<220> FEATURE:
<223> OTHER INFORMATION: Synthetic peptide: CDR3 of the variable region of the heavy chain of H5 SH 2.1

<400> SEQUENCE: 25

Asp Ala Lys Phe Met Ser Asp Gly Ile Gly Phe Asp Tyr
1 5 10

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide: CDR3 of the variable region of the heavy chain of H5 SH 4.1

<400> SEQUENCE: 26

Asp Ala Trp Gly Trp Thr Ile Leu Ser Gly Phe Asp Tyr
1 5 10

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide: CDR3 of the variable region of the heavy chain of H5 SH 5.1

<400> SEQUENCE: 27

Asp Ala Ala Tyr Met Ile Arg Tyr Glu Gly Phe Asp Tyr
1 5 10

<210> SEQ ID NO 28
<211> LENGTH: 13
<212> TYPE: PRT
<213> ORGANISM: Artificial Sequence
<220> FEATURE:
<223> OTHER INFORMATION: Synthetic peptide: CDR3 of the variable region of the heavy chain of H5 SH 2.3

<400> SEQUENCE: 28

Asp Ala Trp Ile Tyr Trp Ala Arg Glu Gly Phe Asp Tyr
1 5 10

<210> SEQ ID NO 29
<211> LENGTH: 13
<212> TYPE: PRT
<213> ORGANISM: Artificial Sequence
<220> FEATURE:
<223> OTHER INFORMATION: Synthetic peptide: CDR3 of the variable region of the heavy chain of H5 SH 3.3

<400> SEQUENCE: 29

Asp Ala Cys Met Thr Tyr Ser Arg Glu Gly Phe Asp Tyr
1 5 10

<210> SEQ ID NO 30
<211> LENGTH: 13
<212> TYPE: PRT

```
<213> ORGANISM: Artificial Sequence
<220> FEATURE:
<223> OTHER INFORMATION: Synthetic peptide: CDR3 of the variable region
      of the heavy chain of H5 SH 5.3

<400> SEQUENCE: 30

Asp Ala Trp Leu Asp Val Leu Ser Asp Gly Phe Asp Tyr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic peptide: CDR3 of the variable region
      of the heavy chain of H5 SH 14.3

<400> SEQUENCE: 31

Asp Ala Pro Ser Val Asn Asp Arg Glu Gly Phe Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of WT FW4.4

<400> SEQUENCE: 32

Gly Thr Trp Asp Ser Ser Leu Ser Gly Val Val
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-9.1

<400> SEQUENCE: 33

Ala Ala Trp Asp Ser Val Lys His Gly Val Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-21.1

<400> SEQUENCE: 34

Ala Ala Trp Asp Asn Ser Met Arg Gly Val Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-22.1

<400> SEQUENCE: 35

Ala Ala Trp Asp Thr Met Arg Tyr Gly Val Val
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-25.1

<400> SEQUENCE: 36

Ala Ala Trp Asp Thr Thr Arg Val Gly Val Val
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-27.1

<400> SEQUENCE: 37

Ala Ser Trp Asp Thr Met Leu Lys Gly Val Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-28.1

<400> SEQUENCE: 38

Ala Ser Trp Asp Thr Pro Thr Cys Gly Val Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-29.1

<400> SEQUENCE: 39

Ala Thr Trp Asp Ile Ser Arg Cys Gly Val Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-46.1

<400> SEQUENCE: 40

Ala Thr Trp Asp Thr Val Cys Ala Gly Val Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-53.1

```
<400> SEQUENCE: 41

Ala Thr Trp Asp Val Asp Val Phe Gly Val Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-57.1

<400> SEQUENCE: 42

Ala Thr Trp Asp Asp Val Val Gly Gly Val Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-86.1

<400> SEQUENCE: 43

Ala Ala Trp Asp Ser Phe Tyr Asn Gly Val Val
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-94.1

<400> SEQUENCE: 44

Ala Ser Trp Asp Thr Leu Ile Glu Gly Val Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-107.1

<400> SEQUENCE: 45

Ala Thr Trp Asp Asn Asp Lys Trp Gly Val Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-112.1

<400> SEQUENCE: 46

Ala Ala Trp Asp Ser Thr Thr Cys Gly Val Val
1               5                   10

<210> SEQ ID NO 47
<211> LENGTH: 11
```

```
<212> TYPE: PRT
<213> ORGANISM: Artificial Sequence
<220> FEATURE:
<223> OTHER INFORMATION: Synthetic peptide: CDR3 of the light chain
      variable region of 5.3-113.1

<400> SEQUENCE: 47

Ala Thr Trp Asp Met Trp Met Lys Gly Val Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-117.1

<400> SEQUENCE: 48

Gly Thr Trp Asp Ser Ser Leu Ser Gly Val Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-118.1

<400> SEQUENCE: 49

Ala Ala Trp Asp Trp Val Leu Gly Gly Val Val
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-6.1

<400> SEQUENCE: 50

Ala Thr Trp Asp Asn Pro Gly Gln Gly Val Val
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-7.1

<400> SEQUENCE: 51

Ala Thr Trp Asp Asp Trp Val Ile Gly Val Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-8.1

<400> SEQUENCE: 52

Ala Ser Trp Asp Asp Gln Lys Trp Gly Val Val
```

<210> SEQ ID NO 53
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-9.1

<400> SEQUENCE: 53

Ala Thr Trp Asp Thr Asn Arg His Gly Val Val
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-12.1

<400> SEQUENCE: 54

Ala Ser Trp Asp Asp Leu His Ile Gly Val Val
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-13.1

<400> SEQUENCE: 55

Ala Ser Trp Asp Glu Glu Ala Trp Gly Val Val
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-21.1

<400> SEQUENCE: 56

Ala Thr Trp Asp Tyr Ile Lys Ile Gly Val Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 14.3-48.1

<400> SEQUENCE: 57

Ala Thr Trp Asp Thr Phe Glu Arg Gly Val Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic peptide: CDR3 of the light chain -continued variable region of 14.3-49.1

<400> SEQUENCE: 58

Ala Thr Trp Asp Ser Asn Leu Ile Gly Val Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-24.,1

<400> SEQUENCE: 59

Ala Thr Trp Asp Asn Asn Thr Cys Gly Val Val
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-3.1

<400> SEQUENCE: 60

Ala Ala Trp Asp Cys Asp Ile Asn Gly Val Val
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-8.1

<400> SEQUENCE: 61

Ala Ser Trp Asp Ser Met Lys Ile Gly Val Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic peptide: CDR3 of the light chain
      variable region of 5.3-19.1

<400> SEQUENCE: 62

Ala Thr Trp Asp Cys Thr Arg Ala Gly Val Val
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv WT (ESBA521)

<400> SEQUENCE: 63

Ala Ile Ser Gly Ser Gly Gly Ser Thr Tyr Tyr Ala Asp Ser Val Lys
1               5                   10                  15

Gly

<210> SEQ ID NO 64
<211> LENGTH: 16
<212> TYPE: PRT
<213> ORGANISM: Artificial Sequence
<220> FEATURE:
<223> OTHER INFORMATION: Synthetic peptide: CDR2 of the heavy chain
      variable region of the scFv 1.1

<400> SEQUENCE: 64

Ala Ile Lys Thr Asp Gly Gln Asn Tyr Tyr Ala Asp Ser Val Lys Gly
1               5                   10                  15

<210> SEQ ID NO 65
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 17.1

<400> SEQUENCE: 65

Ala Ile Arg Ser Asp Gly Asn Glu Arg Tyr Tyr Ala Asp Ser Val Lys
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 35.1

<400> SEQUENCE: 66

Ala Ile Asn Thr Asn Gly Asn Glu Lys Tyr Tyr Ala Asp Ser Val Lys
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 64.1

<400> SEQUENCE: 67

Ala Ile Ser Thr Asn Gly Lys Glu Arg Tyr Tyr Ala Asp Ser Val Lys
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 130.1

<400> SEQUENCE: 68

Ala Ile Arg Thr Gln Ser Gln Glu Glu Tyr Tyr Ala Asp Ser Val Lys
1               5                   10                  15

Gly

```
<210> SEQ ID NO 69
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 152.1

<400> SEQUENCE: 69

Ala Ile Lys Ser Arg Ser Gln Glu Gln Tyr Tyr Ala Asp Ser Val Lys
1               5                   10                  15
Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 167.1

<400> SEQUENCE: 70

Ala Ile Lys Ser His Ser Gln Gln Gln Tyr Tyr Ala Asp Ser Val Lys
1               5                   10                  15
Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 214.1

<400> SEQUENCE: 71

Ala Ile Asn Ser Glu Gly Gln Gln Arg Tyr Tyr Ala Asp Ser Val Lys
1               5                   10                  15
Gly

<210> SEQ ID NO 72
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 225.1

<400> SEQUENCE: 72

Ala Ile Lys Ser Lys Gly Gln Asn Lys Tyr Tyr Ala Asp Ser Val Lys
1               5                   10                  15
Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 262.1

<400> SEQUENCE: 73

Ala Ile Arg Thr Asn Ser Glu Glu Lys Tyr Tyr Ala Asp Ser Val Lys
1               5                   10                  15
Gly
```

<210> SEQ ID NO 74
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 265.1

<400> SEQUENCE: 74

Ala Ile Asn Met Lys Gly Asn Asp Arg Tyr Tyr Ala Asp Ser Val Lys
1               5                   10                  15

Gly

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide: CDR2 of the heavy chain
      variable region of the scFv 43.2

<400> SEQUENCE: 75

Ala Ile Arg Thr Asn Ser Lys Glu Tyr Tyr Ala Asp Ser Val Lys Gly
1               5                   10                  15

<210> SEQ ID NO 76
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 70.2

<400> SEQUENCE: 76

Ala Ile Lys Thr Glu Ser Gln Gln Arg Tyr Tyr Ala Asp Ser Val Lys
1               5                   10                  15

Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 99.2

<400> SEQUENCE: 77

Ala Ile Asn Ser Asn Gly Lys Gln Asp Tyr Tyr Ala Asp Ser Val Lys
1               5                   10                  15

Gly

<210> SEQ ID NO 78
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 100.2

<400> SEQUENCE: 78

Ala Ile Lys Thr Asp Gly Asn His Lys Tyr Tyr Ala Asp Ser Val Lys
1               5                   10                  15

Gly

```
<210> SEQ ID NO 79
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 109.2

<400> SEQUENCE: 79

Ala Ile Asp Thr Lys Gly Asn Gly Gln Tyr Tyr Ala Asp Ser Val Lys
1               5                   10                  15

Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 146.2

<400> SEQUENCE: 80

Ala Ile Arg Ser Asp Ser Ser His Lys Tyr Tyr Ala Asp Ser Val Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 173.2

<400> SEQUENCE: 81

Ala Ile Asn Thr Lys Ser Asn Glu Gln Tyr Tyr Ala Asp Ser Val Lys
1               5                   10                  15

Gly

<210> SEQ ID NO 82
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 199.2

<400> SEQUENCE: 82

Ala Ile Arg Thr Asp Ser Lys Asn Ser Tyr Tyr Ala Asp Ser Val Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 2.11

<400> SEQUENCE: 83

Ala Ile Arg Thr Asp Ser Lys Glu Gln Tyr Tyr Ala Asp Ser Val Lys
1               5                   10                  15

Gly
```

```
<210> SEQ ID NO 84
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 19.11

<400> SEQUENCE: 84

Ala Ile Arg Thr Asn Ser Lys Glu Glu Tyr Tyr Ala Asp Ser Val Lys
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 28.11

<400> SEQUENCE: 85

Ala Ile Glu Thr Ser Ser Gly Ser Thr Tyr Tyr Ala Asp Ser Val Lys
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 33.11

<400> SEQUENCE: 86

Ala Ile Asn Thr Gly Gly Gly Ser Thr Tyr Tyr Ala Asp Ser Val Lys
1               5                   10                  15

Gly

<210> SEQ ID NO 87
<211> LENGTH: 17
<212> TYPE: PRT
<213> ORGANISM: Artificial Sequence
<220> FEATURE:
<223> OTHER INFORMATION: Synthetic peptide: CDR2 of the heavy chain
      variable region of the scFv 4.12

<400> SEQUENCE: 87

Ala Ile Asn Thr Arg Gly Gln Asn Glu Tyr Tyr Ala Asp Ser Val Lys
1               5                   10                  15

Gly

<210> SEQ ID NO 88
<211> LENGTH: 16
<212> TYPE: PRT
<213> ORGANISM: Artificial Sequence
<220> FEATURE:
<223> OTHER INFORMATION: Synthetic peptide: CDR2 of the heavy chain
      variable region of the scFv 6.12

<400> SEQUENCE: 88

Ala Ile Ser Thr Ser Gly Ser Thr Tyr Tyr Ala Asp Ser Val Lys Gly
1               5                   10                  15
```

<210> SEQ ID NO 89
<211> LENGTH: 2520
<212> TYPE: DNA
<213> ORGANISM: Artificial Sequence
<220> FEATURE:
<223> OTHER INFORMATION: Synthetic expression vector pAK400 with the
      ESBA521 coding sequence

<400> SEQUENCE: 89

```
acccgacacc atcgaatggc gcaaaacctt tcgcggtatg gcatgatagc gcccggaaga      60
gagtcaattc agggtggtga atgtgaaacc agtaacgtta tacgatgtcg cagagtatgc     120
cggtgtctct tatcagaccg tttcccgcgt ggtgaaccag gccagccacg tttctgcgaa     180
aacgcgggaa aaagtggaag cggcgatggc ggagctgaat tacattccca accgcgtggc     240
acaacaactg gcgggcaaac agtcgttgct gattggcgtt gccacctcca gtctggccct     300
gcacgcgccg tcgcaaattg tcgcggcgat taaatctcgc gccgatcaac tgggtgccag     360
cgtggtggtg tcgatggtag aacgaagcgg cgtcgaagcc tgtaaagcgg cggtgcacaa     420
tcttctcgcg caacgcgtca gtgggctgat cattaactat ccgctggatg accaggatgc     480
cattgctgtg gaagctgcct gcactaatgt tccggcgtta tttcttgatg tctctgacca     540
gacacccatc aacagtatta ttttctccca tgaagacggg acgcgactgg gcgtggagca     600
tctggtcgca ttgggtcacc agcaaatcgc gctgttagcg ggcccattaa gttctgtctc     660
ggcgcgtctg cgtctggctg ctggcataaa atatctcact cgcaatcaaa ttcagccgat     720
agcggaacgg gaaggcgact ggagtgccat gtccggtttt caacaaacca tgcaaatgct     780
gaatgagggc atcgttccca ctgcgatgct ggttgccaac gatcagatgg cgctgggcgc     840
aatgcgcgcc attaccgagt ccgggctgcg cgttggtgcg acatctcgg tagtgggata      900
cgacgatacc gaagacagct catgttatat cccgccgtta accaccatca acaggatttt     960
tcgcctgctg ggcaaaacca gcgtggaccg cttgctgcaa ctctctcagg ccaggcggt     1020
gaagggcaat cagctgttgc ccgtctcact ggtgaaaaga aaaccaccc tggcgcccaa     1080
tacgcaaacc gcctctcccc gcgcgttggc cgattcatta atgcagctgg cacgacaggt     1140
ttcccgactg gaaagcgggc agtgagcggt accgataaa agcggcttcc tgacaggagg     1200
ccgtttttgtt ttgcagccca cctcaacgca attaatgtga gttagctcac tcattaggca    1260
ccccaggctt tacactttat gcttccggct cgtatgttgt gtggaattgt gagcggataa    1320
caatttcaca caggaaacag ctatgaccat gattacgaat ttctagagaa ggagatatac    1380
atatgaaata cctattgcct acggcagccg ctggattgtt attactcgcg gcccagccgg    1440
ccatggcgga ctacaaagac cagtctgtgc tgacgcagcc gccctcagtg tctgcggccc    1500
caggacagaa ggtcaccatc tcctgctccg gaagcacctc caacattggc gataattatg    1560
tatcctggta ccaacaactc ccaggaacag cccccccaact cctcatttat gacaatacta    1620
aacgaccctc agggattcct gaccggttct ctggctccaa gtctggcacg tcagccaccc    1680
tgggcatcac cggactccag actggggacg aggccgatta ttactgcgcg acctgggata    1740
atgataagtg gggtgtggtt ttcggcggag ggaccaagct cgaggtccta ggtggtggtg    1800
gtggttctgg tggtggtggt tctgcggcg cggctccag tggtggtgga tccgaggtgc    1860
agctggtgga gtccggggga ggcttggtac agcctggggg gtccctgaga ctctcctgtg    1920
cagcctctgg attcaccttt agcagctatg ccatgagctg ggtccgccag gctccaggga    1980
aggggctgga gtgggtctca gctattagtg gtagtggtgg tagcacatac tacgcagact    2040
ccgtgaaggg ccggttcacc atctccagag acaattccaa gaacacgctg tatctgcaaa    2100
```

```
tgaacagcct gagagccgag gacacggccg tatattactg cgcgcgtgat gcgtggttgg    2160
atgtgctttc ggatggcttt gactactggg gccagggaac cctggtcacc gtctcctcgg    2220 cctcggggc cgatcaccat catcaccatc attagtaagc ttgacctgtg aagtgaaaaa    2280
tggcgcacat tgtgcgacat ttttttttgtc tgccgtttac cgctactgcg tcacggatcc    2340
ccacgcgccc tgtagcggcg cattaagcgc ggcgggtgtg gtggttacgc gcagcgtgac    2400
cgctacactt gccagcgccc tagcgcccgc tcctttcgct ttcttccctt cctttctcgc    2460
cacgttcgcc ggctttcccc gtcaagctct aaatcgggc atccctttag ggttccgatt    2520
```

<210> SEQ ID NO 90
<211> LENGTH: 3319
<212> TYPE: DNA
<213> ORGANISM: Artificial Sequence
<220> FEATURE:
<223> OTHER INFORMATION: Synthetic pTFT74 expression vector with ESBA521
      coding sequence

<400> SEQUENCE: 90

```
acccgacacc atcgaaatta atacgactca ctatagggag accacaacgg tttcccgaat      60
tgtgagcgga taacaataga aataattttg tttaactttta agaaggagat atatccatgg    120
cgcagtctgt gctgacgcag ccgcccctcag tgtctgcggc cccaggacag aaggtcacca    180
tctcctgctc cggaagcacc tccaacattg gcgataatta tgtatcctgg taccaacaac    240
tcccaggaac agcccccaa ctcctcattt atgacaatac taaacgaccc tcagggattc    300
ctgaccggtt ctctggctcc aagtctggca cgtcagccac cctgggcatc accggactcc    360
agactgggga cgaggccgat tattactgcg cgacctggga taatgataag tggggtgtgg    420
ttttcggcgg agggaccaag ctcgaggtcc taggtggtgg tggtggttct ggtggtggtg    480
gttctggcgg cggcggctcc agtggtggtg gatccgaggt gcagctggtg gagtccgggg    540
gaggcttggt acagcctggg gggtccctga ctctcctg tgcagcctct ggattcacct    600
ttagcagcta tgccatgagc tgggtccgcc aggctccagg aaggggctg gagtgggtct    660 cagctattag tggtagtggt ggtagcacat actacgcaga ctccgtgaag ggccggttca    720
ccatctccag agacaattcc aagaacacgc tgtatctgca aatgaacagc ctgagagccg    780
aggacacggc cgtatattac tgcgcgcgtg atgcgtggtt ggatgtgctt cggatggct    840 ttgactactg gggccaggga accctggtca ccgtctcctc gtagtaagct tcagtcccgg    900
gcagtggatc cggctgctaa caaagcccga aaggaagctg agttggctgc tgccaccgct    960
gagcaataac tagcataacc ccttggggcc tctaaacggg tcttgagggg ttttttgctg    1020
aaaggaggaa ctatatccgg atcgagatcc ccacgcgccc tgtagcggcg cattaagcgc    1080
ggcgggtgtg gtggttacgc gcagcgtgac cgctacactt gccagcgccc tagcgcccgc    1140
tcctttcgct ttcttccctt cctttctcgc cacgttcgcc ggctttcccc gtcaagctct    1200 aaatcgggc atccctttag ggttccgatt tagtgcttta cggcacctcg accccaaaaa    1260
acttgattag ggtgatggtt cacgtagtgg gccatcgccc tgatagacgg ttttttcgccc    1320 tttgacgttg gagtccacgt tctttaatag tggactcttg ttccaaactg gaacaacact    1380
caaccctatc tcggtctatt cttttgattt ataagggatt tgccgattt cggctattg    1440 gttaaaaaat gagctgattt aacaaaaatt taacgcgaat tttaacaaaa tattaacgtt    1500
tacaatttca ggtggcactt ttcggggaaa tgtgcgcgga accccctattt gtttatttt    1560 ctaaatacat tcaaatatgt atccgctcat gagacaataa ccctgataaa tgcttcaata    1620
```

| | |
|---|---|
| atattgaaaa aggaagagta tgagtattca acatttccgt gtcgcccta ttccctttt | 1680 |
| tgcggcattt tgccttcctg tttttgctca cccagaaacg ctggtgaaag taaaagatgc | 1740 |
| tgaagatcag ttgggtgcac gagtgggtta catcgaactg gatctcaaca gcggtaagat | 1800 |
| ccttgagagt tttcgccccg aagaacgttt tccaatgatg agcactttta aagttctgct | 1860 |
| atgtggcgcg gtattatccc gtattgacgc cgggcaagag caactcggtc gccgcataca | 1920 |
| ctattctcag aatgacttgg ttgagtactc accagtcaca gaaaagcatc ttacggatgg | 1980 |
| catgacagta agagaattat gcagtgctgc cataaccatg agtgataaca ctgcggccaa | 2040 |
| cttacttctg acaacgatcg gaggaccgaa ggagctaacc gcttttttgc acaacatggg | 2100 |
| ggatcatgta actcgccttg atcgttggga accggagctg aatgaagcca taccaaacga | 2160 |
| cgagcgtgac accacgatgc ctgtagcaat ggcaacaacg ttgcgcaaac tattaactgg | 2220 |
| cgaactactt actctagctt cccggcaaca attaatagac tggatggagg cggataaagt | 2280 |
| tgcaggacca cttctgcgct cggcccttcc ggctggctgg tttattgctg ataaatctgg | 2340 |
| agccggtgag cgtgggtctc gcggtatcat tgcagcactg gggccagatg gtaagccctc | 2400 |
| ccgtatcgta gttatctaca cgacggggag tcaggcaact atggatgaac gaaatagaca | 2460 |
| gatcgctgag ataggtgcct cactgattaa gcattggtaa ctgtcagacc aagtttactc | 2520 |
| atatatactt tagattgatt taaaacttca ttttaattt aaaaggatct aggtgaagat | 2580 |
| cctttttgat aatctcatga ccaaaatccc ttaacgtgag ttttcgttcc actgagcgtc | 2640 |
| agaccccgta gaaagatca aaggatcttc ttgagatcct ttttttctgc gcgtaatctg | 2700 |
| ctgcttgcaa acaaaaaaac caccgctacc agcggtggtt tgtttgccgg atcaagagct | 2760 |
| accaactctt tttccgaagg taactggctt cagcagagcg cagataccaa atactgtcct | 2820 |
| tctagtgtag ccgtagttag gccaccactt caagaactct gtagcaccgc ctacatacct | 2880 |
| cgctctgcta atcctgttac cagtggctgc tgccagtggc gataagtcgt gtcttaccgg | 2940 |
| gttggactca agacgatagt taccggataa ggcgcagcgg tcgggctgaa cggggggttc | 3000 |
| gtgcacacag cccagcttgg agcgaacgac ctacaccgaa ctgagatacc tacagcgtga | 3060 |
| gctatgagaa agcgccacgc ttcccgaagg gagaaaggcg acaggtatc cggtaagcgg | 3120 |
| cagggtcgga acaggagagc gcacgaggga gcttccaggg ggaaacgcct ggtatcttta | 3180 |
| tagtcctgtc gggtttcgcc acctctgact tgagcgtcga ttttgtgat gctcgtcagg | 3240 |
| ggggcggagc ctatggaaaa acgccagcaa cgcggccttt ttacggttcc tggccttttg | 3300 |
| ctggcctttt gctcacatg | 3319 |

<210> SEQ ID NO 91
<211> LENGTH: 22
<212> TYPE: PRT
<213> ORGANISM: Homo sapiens

<400> SEQUENCE: 91

Val Leu Gln Gly Arg Ile Gly Arg Pro Asp Asn Pro Phe Arg Val Ala
1               5                   10                  15

Leu Glu Tyr Ile Ser Ser
            20

<210> SEQ ID NO 92
<211> LENGTH: 18
<212> TYPE: PRT
<213> ORGANISM: Artificial Sequence
<220> FEATURE:

```
<223> OTHER INFORMATION: Synthetic peptide: FW4.4 VH CDR3

<400> SEQUENCE: 92

Cys Ala Arg Asp Ala Gly Ile Ala Val Ala Gly Thr Gly Phe Asp Tyr
1               5                   10                  15

Trp Gly

<210> SEQ ID NO 93
<211> LENGTH: 18
<212> TYPE: PRT
<213> ORGANISM: Artificial Sequence
<220> FEATURE:
<223> OTHER INFORMATION: Synthetic peptide: Consensus VH CDR3
<220> FEATURE:
<221> NAME/KEY: misc_feature
<222> LOCATION: (6)..(12)
<223> OTHER INFORMATION: Xaa can be any naturally occurring amino acid

<400> SEQUENCE: 93

Cys Ala Arg Asp Ala Xaa Xaa Xaa Xaa Xaa Xaa Xaa Gly Phe Asp Tyr
1               5                   10                  15

Trp Gly

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide: FW4.4 VL CDR3

<400> SEQUENCE: 94

Tyr Cys Gly Thr Trp Asp Ser Ser Leu Ser Gly Val Val Phe Gly
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide: Consensus VL CDR3
<220> FEATURE:
<221> NAME/KEY: misc_feature
<222> LOCATION: (3)..(3)
<223> OTHER INFORMATION: Xaa is Ala, Gly, or Gln
<220> FEATURE:
<221> NAME/KEY: misc_feature
<222> LOCATION: (4)..(4)
<223> OTHER INFORMATION: Xaa is Ser, Ala, or Thr
<220> FEATURE:
<221> NAME/KEY: misc_feature
<222> LOCATION: (7)..(10)
<223> OTHER INFORMATION: Xaa can be any naturally occurring amino acid

<400> SEQUENCE: 95

Tyr Cys Xaa Xaa Trp Asp Xaa Xaa Xaa Xaa Gly Val Val Phe Gly
1               5                   10                  15

<210> SEQ ID NO 96
<211> LENGTH: 21
<212> TYPE: PRT
<213> ORGANISM: Artificial Sequence
<220> FEATURE:
<223> OTHER INFORMATION: Synthetic peptide: FW4.4 VH CDR2

<400> SEQUENCE: 96

Val Ser Ala Ile Ser Gly Ser Gly Gly Ser Thr Tyr Tyr Ala Asp Ser
1               5                   10                  15
```

Val Lys Gly Arg Phe
            20

<210> SEQ ID NO 97
<211> LENGTH: 21
<212> TYPE: PRT
<213> ORGANISM: Artificial Sequence
<220> FEATURE:
<223> OTHER INFORMATION: Synthetic peptide: Consensus VH CDR2
<220> FEATURE:
<221> NAME/KEY: misc_feature
<222> LOCATION: (5)..(5)
<223> OTHER INFORMATION: Xaa is His, Gln, Asn, Lys, Asp, Glu, Arg, Ser,
      or Gly
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is His, Gln, Asn, Lys, Asp, Glu, Arg, Ser,
      or Gly
<220> FEATURE:
<221> NAME/KEY: misc_feature
<222> LOCATION: (8)..(8)
<223> OTHER INFORMATION: Xaa is Gly or Ser
<220> FEATURE:
<221> NAME/KEY: misc_feature
<222> LOCATION: (9)..(11)
<223> OTHER INFORMATION: Xaa is His, Gln, Asn, Lys, Asp, Glu, Arg, Ser,
      or Gly

<400> SEQUENCE: 97

Val Ser Ala Ile Xaa Xaa Xaa Xaa Xaa Xaa Xaa Tyr Tyr Ala Asp Ser
1               5                   10                  15

Val Lys Gly Arg Phe
            20

<210> SEQ ID NO 98
<211> LENGTH: 13
<212> TYPE: PRT
<213> ORGANISM: Artificial Sequence
<220> FEATURE:
<223> OTHER INFORMATION: Synthetic peptide: Consensus VH CDR3
<220> FEATURE:
<221> NAME/KEY: misc_feature
<222> LOCATION: (3)..(9)
<223> OTHER INFORMATION: Xaa can be any naturally occurring amino acid

<400> SEQUENCE: 98

Asp Ala Xaa Xaa Xaa Xaa Xaa Xaa Xaa Gly Phe Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic peptide: Consensus VL CDR3
<220> FEATURE:
<221> NAME/KEY: misc_feature
<222> LOCATION: (1)..(1)
<223> OTHER INFORMATION: Xaa is Gly, Ala or Gln
<220> FEATURE:
<221> NAME/KEY: misc_feature
<222> LOCATION: (2)..(2)
<223> OTHER INFORMATION: Xaa is Thr, Ser or Ala
<220> FEATURE:
<221> NAME/KEY: misc_feature
<222> LOCATION: (5)..(8)
<223> OTHER INFORMATION: Xaa can be any naturally occurring amino acid

```
<400> SEQUENCE: 99

Xaa Xaa Trp Asp Xaa Xaa Xaa Xaa Gly Val Val
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Synthetic peptide: Consensus VH CDR2
<220> FEATURE:
<221> NAME/KEY: misc_feature
<222> LOCATION: (3)..(3)
<223> OTHER INFORMATION: Xaa is His, Gln, Asn, Lys, Asp, Glu, Arg, Ser,
      or Gly
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is His, Gln, Asn, Lys, Asp, Glu, Arg, Ser,
      or Gly
<220> FEATURE:
<221> NAME/KEY: misc_feature
<222> LOCATION: (6)..(6)
<223> OTHER INFORMATION: Xaa is Gly or Ser
<220> FEATURE:
<221> NAME/KEY: misc_feature
<222> LOCATION: (7)..(9)
<223> OTHER INFORMATION: Xaa is His, Gln, Asn, Lys, Asp, Glu, Arg, Ser,
      or Gly

<400> SEQUENCE: 100

Ala Ile Xaa Xaa Xaa Xaa Xaa Xaa Xaa Tyr Tyr Ala Asp Ser Val Lys
1               5                   10                  15

Gly
```

METHOD FOR TREATING GLIOBLASTOMA USING ANTIBODIES BINDING TO THE EXTRACELLULAR DOMAIN OF THE RECEPTOR TYROSINE KINASE ALK

RELATED INFORMATION

This application is a divisional of U.S. patent application Ser. No. 11/796,549, filed Apr. 27, 2007, now U.S. Pat. No. 7,902,340, which claims priority to U.S. provisional patent application No. 60/795,831, filed Apr. 28, 2006, the entire contents of which are hereby incorporated by reference.

The contents of any patents, patent applications, and references cited throughout this specification are hereby incorporated by reference in their entireties.

TECHNICAL FIELD

The present invention concerns an antibody specific for human ALK (Anaplastic Lymphoma Kinase), in particular a scFv, a nucleic acid sequence encoding it, its production and its use as a pharmaceutical or for diagnostic purposes. Said antibody is suitable for the local treatment of tumors or cancer, in particular glioblastoma.

BACKGROUND ART

ALK (Anaplastic Lymphoma Kinase; CD246) is a member of the receptor tyrosine kinase (RTK) family. As a typical member of this family, it is a type-I transmembrane protein essentially consisting of three domains: the extracellular ligand-binding domain (aa19-1038), which contains one LDL-receptor class A domain and two MAM domains (MAM: Meprin, A5 antigen, protein tyrosine phosphatase µ), a transmembrane domain (aa1039-1059) and a cytoplasmic domain (aa 1060-1620), containing the tyrosine kinase domain. A signal peptide is present at the N-terminus of the nascent protein (aa 1-18), which is cleaved upon secretion.

The full-length human and mouse ALK were cloned in 1997 by two independent groups (Iwahara 1997; Morris 1997). ALK is highly similar to the RTK called Leukocyte Tyrosine Kinase (LTK) and belongs to the insulin receptor superfamily. ALK exhibits 57% aa identity and 71% aa similarity with LTK in their regions of overlap (Morris 2001). ALK is highly N-glycosylated and contains 21 putative N-glycosylation sites. Amino acids 687 to 1034 have significant similarity (50% aa identity) to LTK. However, the N-terminus proximal 686 aa sequence shows no homology to any known proteins with the exception of a very short sequence also found in the LDL receptor (Duyster 2001/SWISSPROT). In addition, it contains two MAM domains at aa264-427 and aa478-636 (Meprin, A5 antigen, protein tyrosine phosphatase µ). These domains are thought to have an adhesive function, as they are widespread among various adhesive proteins implicated in cell-to-cell interaction (De Juan 2002). Furthermore, there is a binding site for the ALK putative ligands corresponding to amino acids 396-406 (Stoica 2001; see below). The amino acid sequence of the kinase domain of murine ALK shows 98% aa-identity to human ALK, 78% identity to mouse LTK, 52% to mouse ros, 47% to human insulin-like growth factor receptor and 46% to human insulin receptor (Iwahara 1997; Ladanyi 2000). No splice variants of ALK have been described to date. However, ALK is often associated with chromosomal translocations (see below).

The ALK gene spans about 315 kb and has 26 exons. Much of the gene consists of two large introns that span about 170 kb. The ALK transcript is 6.5 kb of length (Kutok 2002). According to Morris, the cDNA spans 6226 bp (Morris 2001).

ALK expression in mice starts during embryogenesis around the development stage E11 and is persisting in the neonatal periods of development where it is expressed in the nervous system. In the adult, its physiological expression is restricted to certain neuronal (neural and glial cells and probably endothelial cells) regions of the CNS at low levels (Morris 1997; Duyster 2001; Stoica 2001). Actually, the abundance of ALK decreases in the postnatal period (Morris 2001). Based on its expression pattern, a role for the receptor in brain development is suggested (Duyster 2001). The neural-restricted expression of ALK suggests that it serves as a receptor for neurotrophic factors (see later). Consistent with this, its expression pattern overlaps with the genes encoding the TRK family of neurotrophin receptors (Morris 2001). However, ALK knockout mice do not show any obvious phenotype (unpublished data), which might be due to some functional redundancy with TRK family members or other neurotrophin receptors. Notably, hematopoietic tissues show no detectable expression of ALK (see Morris 2001).

Two potential ligands for ALK have recently been described, "pleiotrophin" (PTN) and "midkine" (MK) (Stoica 2001; Duyster 2001; Stoica 2002). The PTN-ALK interaction was identified by using purified human pleiotrophin protein to screen a phage display peptide library. By this method, a sequence of ALK present in its extracellular domain (aa 396-406) was identified. Importantly, this sequence is not shared with LTK, the RTK most closely related to ALK. This ligand-binding region is also conserved in the potential homologue of ALK in *Drosophila* (Loren 2001). ALK is phosphorylated rapidly upon PTN binding (Bowden 2002). Moreover, ALK has been shown to be stimulated by pleiotrophin in cell culture. This makes the pleiotrophin/ALK interaction particularly interesting in the light of the pathological implications pleiotrophin has (Stoica 2001). Cell lines that lack ALK expression also fail to show a growth response to pleiotrophin and vice versa (Stoica 2001). In vivo, elevated pleiotrophin levels in the serum of patients suffering from various solid tumors have been demonstrated, and animal studies have suggested a contribution of pleiotrophin to tumor growth (Stoica 2001). The role of PTN as rate-limiting angiogenic factor in tumor growth is well established in animal models (Choudhuri 1997). In 1996 Czubayko et al. demonstrated the importance of PTN in tumor angiogenesis, in prevention of apoptosis and metastasis by modulating PTN levels with a ribozyme targeting approach (Czubayko 1996). Serum level measurements of PTN in mice demonstrated a clear correlation with the size of the tumor. PTN plays a significant role in some of the most aggressive human cancer types such as melanoma and pancreatic cancer thus giving interesting perspectives for potential further applications of an ALK inhibitor (Weber 2000; Stoica 2001). In human patients, elevated serum pleiotrophin levels were found in patients with pancreatic cancer (n=41; P<0.0001) and colon cancer (n=65; P=0.0079). In healthy individuals, PTN is expressed in a tightly regulated manner during perinatal organ development and in selective populations of neurons and glia in the adult.

Co-expression of PTN and ALK, as found in several cancer cell lines, indicates that they could form an autocrine loop of growth stimulation (Stoica 2001). In spite of all these data, the literature indicates that is not yet clear if the effects of PTN are mediated by ALK alone and/or by other unidentified PTN receptors (Duyster 2001). At least two other potential receptors of PTN have been suggested: the receptor tyrosine phosphatase RPTPβ and the heparan sulfate proteoglycan N-syndecan. However, RPTPβ might act as a signalling modulator of PTN/ALK signalling and N-syndecan as a chaperone for the ligand (Bowden 2002).

Recently, another secreted growth factor related to pleiotrophin called midkine (MK) has been identified as a second ligand for ALK. Similarly to PTN, binding and activating functions (e.g. induction of soft agar colony formation in cell cultures) of MK can be blocked by the same antibody raised against the ALK-ECD (Stoica 2001). Like pleiotrophin, midkine is upregulated in many tumors, although its physiological expression is very restricted in adult normal tissues (Stoica 2002). Analysis of 47 bladder tumor samples revealed that MK expression is significantly (about four times) enhanced as compared to normal bladder tissue. Furthermore, pronounced overexpression correlates with poor patient survival (O'Brien 1996).

However, the affinity of MK for ALK is about 5 times lower than the one of pleiotrophin (Stoica 2002). Interestingly, as with pleiotrophin, inhibition of ALK via ribozymes also inhibits the effects of MK in cell culture (Stoica 2002). The authors of these studies also come to the conclusion that inhibition of the PTK/MK/ALK pathway opens very attractive possibilities for the treatment of various diseases, some of them having very limited treatment options so far, such as, for example, glioblastoma and pancreatic cancer. (Stoica 2002).

In healthy individuals, ALK mRNA expression peaks during the neonatal period and persists in adults in a few selected portions of the nervous system. Recently, expression of the ALK protein was also detected in endothelial cells that were associated to neuronal and glial cells. Evidence that at least a part of the malignant activities described for pleiotrophin are mediated through ALK came from experiments in which the expression of ALK was depleted by a ribozyme targeting approach. Such depletion of ALK prevented pleiotrophin-stimulated phosphorylation of the anti-apoptotic protein Akt and led to a prolonged survival of mice that had received xenografts. Indeed, the number of apoptotic cells in the tumor grafts was significantly increased, when ALK expression was depleted (Powers 2002).

Evidence that malignant activities described for MK are mediated through ALK came from experiments with monoclonal antibodies directed against the ALK ECD. Addition of a 1:25 dilution of hybridoma cell supernatant from two anti-ALK ECD antibodies leads to a significant decrease in colony formation of SW-13 cells in soft agar (Stoica 2002). Analysis of ten different cell lines revealed that the ability for a growth response to PTN perfectly correlated with the expression of ALK mRNA (the following cell lines responded to PTN and were found to express ALK mRNA: HUVEC, NIH3T3, SW-13, Colo357, ME-180, U87, MD-MB 231; Stoica 2001). Interestingly, in some cancer cell lines (Colo357 pancreatic cancer, Hs578T breast cancer and U87 glioblastoma), PTN and ALK are co-expressed, indicating that PTN and ALK form an autocrine loop of growth stimulation (Stoica 2001).

Interestingly, both PTN and MK have been shown to cause transcriptional up-regulation of the anti-apoptotic bcl-2 protein (Stoica 2002). In addition activated Akt (which is a crucial downstream target of aberrant ALK signalling) phosphorylates the pro-apoptotic factor called bad, thus leading to dissociation from bcl-xl, which, when liberated from bad, can suppress apoptosis by blocking the release of cytochrome c (see Bowden 2002 for references).

Aberrant expression of ALK might be involved in the development of several cancers. However, it was first associated with a subgroup of high-malignant Non-Hodgkin lymphomas (NHLs), the so-called Anaplastic Large Cell Lymphomas (ALCLs). Non-Hodgkin lymphomas represent clonal neoplasias originating from various cells of lymphatic origin.

Most patients with the primary systemic clinical subtype of ALCL have the t2,5 translocation, expressing a fusion protein that joins the N-terminus of nucleophosmin (NPM) to the C-terminus of ALK. The fusion consists of aa 1-117 of NPM fused to aa 1058-1620 of ALK and the chromosomal breakage is located in an intron located between the exons encoding the TM and juxtamembrane domain of ALK (Duyster 2001). NPM-ALK is a transcript containing an ORF of 2040 bp encoding a 680aa protein (Morris 2001). This corresponds to a breakage in intron 4 of NPM, which spans 911 bp and intron 16 of ALK which spans 2094 bp (Kutok 2002). Most likely the ALK sequence in this fusion protein is the minimal sequence required for the protein to lead to ALCL (Duyster 2001). The inverse fusion (ALK-NPM) is not expressed, at least not in lymphoid cells (Kutok 2002). The wild-type NPM protein demonstrates ubiquitous expression and functions as a carrier of proteins from the cytoplasm into the nucleolus. As a matter of fact, NPM is a 38 kDa nuclear protein encoded on chromosome 5 that contains a NLS, binds nuclear proteins and engages in cytoplasm/nuclear trafficking (Duyster 2001). NPM is one of the most abundant nucleolar proteins and is normally present as a hexamer (Morris 2001). Most importantly NPM normally undergoes self-oligomerization (hexamers) as well as hetero-oligomerization with NPM-ALK (Duyster 2001). The 2;5 translocation brings the ALK gene portion encoding the tyrosine kinase on chromosome 2 under the control of the strong NPM promoter on chromosome 5, producing permanent expression of the chimeric NPM-ALK protein (p80) (Duyster 2001). Hence, ALK kinase is deregulated and ectopic, both in terms of cell type (lymphoid) and cellular compartment (nucleus/nucleolus and cytoplasm) (Ladanyi 2000). The localization (cytoplasm or nucleus) of NPM seems not to affect its effect on lymphomagenesis (Duyster 2001). The resultant aberrant tyrosine kinase activity triggers malignant transformation via constitutive phosphorylation of intracellular targets. Various other less common ALK fusion proteins are associated with ALCL. All variants demonstrate linkage of the ALK tyrosine kinase domain to an alternative promoter that regulates its expression.

Full-length ALK has been reported to be also expressed in about 92% of primary neuroblastoma cells and in some rhabdomyosarcomas (Lamant 2000). However, no correlation between ALK expression and tumor biology has been demonstrated so far. This fact, taken together with the lack of evidence regarding significant levels of endogenously phosphorylated ALK in these tumors, suggest that ALK expression in neuroblastoma reflects its normal expression in immature neural cells rather than a primary oncogenic role and ALK in these tumors is not constitutively phosphorylated thus questioning an important role for ALK in these tumors (Duyster 2001; Pulford 2001). Nevertheless, ALK signalling might be important in at least some neuroblastomas, as suggested by Miyake et al., who found overexpression and constitutive phosphorylation of ALK due to gene amplification in neuroblastoma-derived cell lines (Miyake 2002). However, other neuroblastoma-derived cell lines do not show constitutive activation of ALK, thus arguing against a general pathological involvement of ALK (Dirks 2002; Pulford 2004).

Most interestingly, ALK seems to be important for growth of glioblastoma multiforme, a highly malignant brain tumor that offers very limited therapeutic options (Powers 2002). Multiple genetic alterations have been shown to occur in these devastating tumors including loss or mutations of PTEN, p53 and INK4a-ARF. In addition, RTK signalling plays a particularly important role in growth and development of these tumors, which overexpress various growth factors such as PDGF, HGF, NGF and VEGF suggesting autocrine RTK signalling loops. Powers and colleagues have shown mRNA and protein expression of ALK in glioblastoma patient tumor samples, whereas the signals were not detectable in normal adjacent brain tissue (Powers 2002). Furthermore, human U87MG glioblastoma cells (which are derived from a patient and represent a well-characterized model system to study tumorigenesis and signalling in glioblastoma) show ALK-dependent anti-apoptotic behaviour in xenograft studies. When ALK is depleted in these tumor cells by the use of ribozymes, mice injected with these tumor cells survive at least twice as long as when injected with wild-type tumor cells, and these tumor cells show drastically increased apoptosis. Thus, ALK and its ligand(s) provide an essential survival signal that is rate-limiting for tumor growth of U87MG cells in vivo (Powers 2002). These finding indicate that inhibition of ALK signalling could be a promising approach to improve life expectancy of glioblastoma patients.

Glioblastoma multiforme is by far the most common and malignant primary glial tumor with an incidence of about 2/100,000/y (about 15,000 cases in US and Western Europe per year). It affects preferentially the cerebral hemispheres, but can also affect the brain stem (mainly in children) or the spinal cord. The tumors may manifest de novo (primary glioblastoma) or may develop from lower grade astrocytomas (secondary glioblastoma). Primary and secondary glioblastomas show little molecular overlap and constitute different disease entities on molecular level. They both contain many genetic abnormalities including affection of p53, EGFR, MDM2, PDGF, PTEN, p16, RB.

No significant therapy advancement has occurred in the last 25 years. Therapies are only palliative and can expand the life expectance from 3 months to 1 year. Patients usually present with slowly progressive neurological deficit, e.g. motor weakness, intracranial pressure symptoms, e.g. headache, nausea, vomiting, cognitive impairment, or seizures. Changes in personality can also be early signs. The etiology of glioblastoma is unknown, familial cases represent less than 1%. The only consistent risk factor identified is exposure to petrochemicals. Diagnosis is made mainly by imaging studies (CT, NMR) and biopsy. Completely staging most glioblastomas is neither practical nor possible because these tumors do not have clearly defined margins. Rather they exhibit well-known tendencies to invade locally and spread along compact white matter pathways. The primary reason why no curative treatment is possible is because the tumor is beyond the reach of local control when diagnosed. The primary chemotherapeutic agents are carmustine (an alkylating agent) and cis-platinum but only 40% of patients show some response.

Although there are quite some uncertainties regarding the role of ALK in glioblastoma, this disease offers various approaches for ALK-directed drugs. In fact, for this devastating disease even a small improvement of current therapy options would serve an enormous medical need. It is important to note that since glioblastoma cells express the full-length ALK, for treating this cancer ALK could be considered as a target not only for small molecule kinase inhibitors but also for antibodies and/or antibody fragments such as scFvs, i.e. to induce apoptosis of tumor cells. The strict localization of glioblastoma to the CNS supports the use of scFvs, if they can be delivered efficiently to the CNS (no rapid clearance due to compartmentalization, but better tumor penetration compared to IgGs due to their smaller size). Antibodies and/or antibody fragments could be directed against the ligand-binding sequence of ALK (aa 396-406) or against other parts of the extracellular parts of the receptor.

The very limited expression of ALK in healthy tissues under physiological conditions indicates that tumors expressing ALK might be an excellent target for disease treatment using radioactive or toxin-labelled antibodies and/or antibody fragments, irrespective of whether ALK is involved in the pathogenesis of these tumors or not. In addition to glioblastoma cells, ALK expression has been found with high significance in melanoma cell lines and breast carcinoma cell lines (without being constitutively phosphorylated) (Dirks 2002). The fact that a large portion of the extracellular domain of ALK seems to be rather unique in the human proteome should make this approach highly specific.

WO9515331/U.S. Pat. No. 5,529,925 discloses the cloning and sequencing of the human nucleic acid sequences, which are rearranged in the t(2;5)(p23;q35) chromosomal translocation event which occurs in human t(2;5) lymphoma. The rearrangement was found to bring sequences from the nucleolar phosphoprotein gene (the NPM gene) on chromosome 5q35 to those from a previously unidentified protein tyrosine kinase gene (hereinafter the ALK gene) on chromosome 2p23. The sequence of the fusion gene and fusion protein (NPM/ALK fusion gene or protein, respectively) were also disclosed.

The full-length ALK sequence is patented in U.S. Pat. No. 5,770,421, entitled "Human ALK Protein Tyrosine Kinase." Furthermore, the U.S. Pat. No. 6,174,674B1 entitled "Method of detecting a chromosomal rearrangement involving a breakpoint in the ALK or NPM gene", discloses primers for detecting the NPM-ALK fusion sequence in patient samples. In another patent, U.S. Pat. No. 6,696,548 entitled "ALK protein tyrosine kinase/receptor and ligands thereof", the use of ALK for detection of ALK ligands and antibodies binding to specific sequences of ALK is disclosed. It also discloses a method of identifying an agent capable of binding to the isolated ALK polypeptide. WO0196394/US20020034768 discloses ALK as receptor of pleiotrophin. US20040234519 discloses anti-pleiotrophin antibodies, and WO2006020684 describes the detection of pleitrophin.

DISCLOSURE OF THE INVENTION

Hence, it is a general object of the invention to provide a stable and soluble antibody or antibody derivative, which binds the human ALK protein in vitro and in vivo. Most preferably, the antibody is specifically targeted against the ligand-binding domain of ALK (amino acids 396-406) and hence will block both the biologic effects of MK, which has a Kd for ALK of about 170 pM, as well as the biologic effects of PTN, which has a Kd for ALK of about 20-30 pM (Stoica 2002; Stoica 2001). In a preferred embodiment said antibody or antibody fragment is a scFv antibody or a Fab fragment. In the following the term antibody comprises full-length antibodies as well as other antibody derivatives.

Now, in order to implement these and still further objects of the invention, which will become more readily apparent as the description proceeds, said antibody is manifested by the features that it comprises a variable heavy chain CDR3 of a sequence of at least 50% identity to the sequence SEQ. ID. No. 2. Preferably, the sequence identity is at least 60%, 65%, 75%, 85%, or more preferably at least 92%. Most preferably, said antibody has a VH CDR3 of the sequence SEQ. ID. No. 2.

In one embodiment, the antibody or antigen binding portion thereof of the invention specifically binds to a particular epitope of the ALK protein. Such epitopes reside, for example, within amino acids 1-50, 50-100, 100-150, 150-200, 200-250, 250-300, 300-350, 350-400, 400-450, 450-500, 500-550, 550-600, 600-650, 650-700, 700-750, 750-800, 800-900, 900-1000, 1000-1100, 1100-1200, 1200-1300, 1300-1400, 1400-1500, or 1500-1620 of the ALK protein, or any interval, portion or range thereof. In one embodiment, the antibody or antigen binding portion thereof specifically binds to an epitope comprising, essentially consisting of or a fragment of the region spanning amino acid residues 391±3 and 406±3 (SEQ. ID No: 91 shows amino acid residues 388 to 409 of the human ALK protein), preferably amino acids 391-406 (SEQ. ID. NO: 1) of the ALK protein (SEQ ID NO: 1). It is understood that the indicated range is not to be considered as having sharp boundaries, but that the antibody or antigen binding portion thereof may bind or partially bind in a region closely situated to or within the ligand-binding domain of ALK. Preferably, the antibodies or antibody-derivatives bind to an epitope of the ALK protein of 10 to 20 amino acids in length.

In another embodiment the antibody or antigen binding portion thereof can be characterized as specifically binding to an ALK protein with a $K_D$ of less than about $10 \times 10^{-6}$ M. In a particular embodiment, the antibody or antigen binding portion thereof specifically binds to an ALK protein (or fragment thereof) with a $K_D$ of at least about $10 \times 10^{-7}$ M, at least about $10 \times 10^{-8}$ M, at least about $10 \times 10^{-9}$ M, at least about $10 \times 10^{-10}$ M, at least about $10 \times 10^{-11}$ M, or at least about $10 \times 10^{-12}$ M or a $K_D$ even more favorable.

In various other embodiments, the antibody or antigen binding portion thereof includes a variable heavy chain region comprising an amino acid sequence at least 80%, 85%, 90%, 95%, 98%, or more preferably at least 99% identical to a variable heavy chain region amino acid sequence as set forth in SEQ ID NO: 4.

In other embodiments, the antibody or antigen binding portion thereof includes a variable light chain region comprising an amino acid sequence at least 80%, 85%, 90%, 95%, 98% or more preferably at least 99% identical to a variable light chain region amino acid sequence as set forth in SEQ ID NO: 5.

In still other embodiments, the antibody or antigen binding portion thereof includes both a variable heavy chain region comprising an amino acid sequence at least 80%, 85%, 90%, 95%, 98% or more preferably at least 99% identical to a variable heavy chain region amino acid sequence as set forth in SEQ ID NO: 4 and a variable light chain region comprising an amino acid sequence at least 80%, 85%, 90%, 95%, 98% or more preferably at least 99% identical to a variable light chain amino acid sequence as set forth in SEQ ID NO: 5.

In certain other embodiments, the antibody or antigen binding portion thereof specifically bind to an epitope that overlaps with an epitope bound by an antibody or antibody derivative of ESBA521 (Seq. ID. No. 19) and/or competes for binding to an ALK protein, or portion thereof, with an antibody or antibody derivative of ESBA521. In a related embodiment, the antibody or antigen binding portion thereof specifically binds to an epitope comprising residues 391-406 (SEQ ID NO: 1) of an ALK protein, or portion thereof.

The variable heavy and light chain regions of the antibodies or antigen binding portions thereof typically include one or more complementarity determining regions (CDRs). These include the CDR1, CDR2, and CDR3 regions. In particular embodiments, the variable heavy chain CDRs are at least 80%, 85%, 90%, 95%, or more preferably 100% identical to a CDR of the ESBA521 antibody. In other particular embodiments, variable light chain CDRs are at least 80%, 85%, 90%, 95%, or more preferably 100%, identical to a CDR of a variable light chain region of the ESBA521 antibody.

Accordingly, particular antibodies or fragments of the invention comprise a variable heavy chain region that includes one or more complementarity determining regions (CDRs) that are at least 80%, 85%, 90%, 95%, or more preferably 100%, identical to a CDR of a variable heavy chain region of the ESBA521 and a variable light chain region that includes one or more CDRs that are at least 80%, 85%, 90%, 95% or more preferably 100%, identical to a CDR of a variable light chain region of the ESBA521 antibody.

The variable heavy chain region of the antibodies or antigen binding portions thereof can also include all three CDRs that are at least 80%, 85%, 90%, 95%, or more preferably 100%, identical to the CDRs of the variable heavy chain region of the ESBA521 antibody and/or all three CDRs that are at least 80%, 85%, 90%, 95% or more preferably 100%, identical to the CDRs of the variable light chain region of the ESBA521 antibody.

In another embodiment of the invention, the antibodies or antigen binding portions thereof (a) include a heavy chain variable region that is encoded by or derived from (i.e. is the product of) a human VH gene (e.g., H3 type); and/or (b) include a light chain variable region that is encoded by or derived from a human V kappa or lambda gene (e.g., lambda1 type).

The antibodies of the present invention include full-length antibodies, for example, monoclonal antibodies, that include an effector domain, (e.g., an Fc domain), as well as antibody portions or fragments, such as single-chain antibodies and Fab fragments. The antibodies can also be linked to a variety of therapeutic agents (e.g., anticancer agents, chemotherapeutics, or toxins) and/or a label (e.g., radiolabel).

In another aspect, the invention features isolated nucleic acids including a sequence encoding an antibody heavy chain variable region which is at least 75%, 80%, 85%, 90%, 95%, or more preferably at least 99%, identical to SEQ ID NO: 22. The invention also features isolated nucleic acids that include a sequence encoding an antibody light chain variable region which is at least 75%, 80%, 85%, 90%, 95%, or more preferably at least 99%, identical to SEQ ID NO: 21.

The invention also features expression vectors including any of the foregoing nucleic acids either alone or in combination (e.g., expressed from one or more vectors), as well as host cells comprising such expression vectors.

Suitable host cells for expressing antibodies of the invention include a variety of eukaryotic cells, e.g., yeast cells, mammalian cells, e.g., Chinese hamster ovary (CHO) cells, NS0 cells, myeloma cells, or plant cells. The molecules of the invention can also be expressed in prokaryotic cells, e.g., *E. coli*.

The invention also features methods for making the antibodies or antigen binding portions thereof by expressing nucleic acids encoding antibodies in a host cell (e.g., nucleic acids encoding the antigen binding region portion of an antibody). In yet another aspect, the invention features a hybridoma or transfectoma including the aforementioned nucleic acids.

In another embodiment, the invention provides an antigen comprising an epitope of the ALK protein, preferably of the PTN ligand binding domain, more preferably a fragment comprising, essentially consisting of or a fragment of the region spanning amino acid residues 391±3 and 406±3 (see SEQ. ID No: 91 which shows amino acid residues 388 to 409 of the human ALK protein), most preferably amino acids 391-406 (SEQ. ID. No: 1). The antigen can be used for raising, screening, or detecting the presence of an anti-ALK antibody or can be used as an agent in active immunotherapy, i.e. as a vaccine.

As a vaccine, the antigen can be used alone or in combination with an appropriate adjuvant or hapten, e.g., mixed or conjugated either chemically or genetically. The antigen when used for active immunotherapy can also be used in combination with passive immunotherapy, for example, with any of the anti-ALK antibodies disclosed herein, or in combination with a monoclonal or polyclonal preparation of anti-ALK antibodies, e.g., serum gammaglobulin from a seropositive donor.

In another embodiment, the antibody molecules (or VL and VH binding regions) are fully human. Treatment of humans with human monoclonal antibodies offers several advantages. For example, the antibodies are likely to be less immunogenic in humans than non-human antibodies. The therapy is also rapid because ALK inactivation can occur as soon as the antibody reaches a cancer site (where ALK is expressed). Therefore, in a related embodiment, the antibody is a scFv antibody, i.e., ESBA521 or an antibody comprising a VL and/or VH region(s) (or CDRs thereof; e.g., VL CDR3 (SEQ ID NO:3) and/or VH CDR3 (SEQ ID NO: 2)) of ESBA521.

Human antibodies also localize to appropriate sites in humans more efficiently than non-human antibodies. Furthermore, the treatment is specific for ALK, is recombinant and highly purified and, unlike traditional therapies, avoids the potential of being contaminated with adventitious agents. Alternatively, antibodies and antibody-derivatives of the present invention may be produced by chemical synthesis.

In another embodiment, the invention provides compositions for treating a cancer (or the making of a medicament so suited) that can prevent neoplasia in a subject by competing with ligands of ALK such as midkine (MK) and/or pleiotrophin (PTN) and thereby block ALK-signaling mediated by such ligands. Such a composition can be administered alone or in combination with art recognized anti-cancer agents, for example, methotrexate, and the like.

The antibody of the invention and/or ALK vaccine can be used alone or in combined with a known therapeutic, e.g., an anti-cancer agent, e.g., methotrexate and the like.

Other features and advantages of the invention will be apparent from the following detailed description, and from the claims.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 3 shows an ELISA experiment wherein the binding characteristics of improved scFvs are compared to that of the framework they originate from.

DETAILED DESCRIPTION OF THE INVENTION

Figure 1:
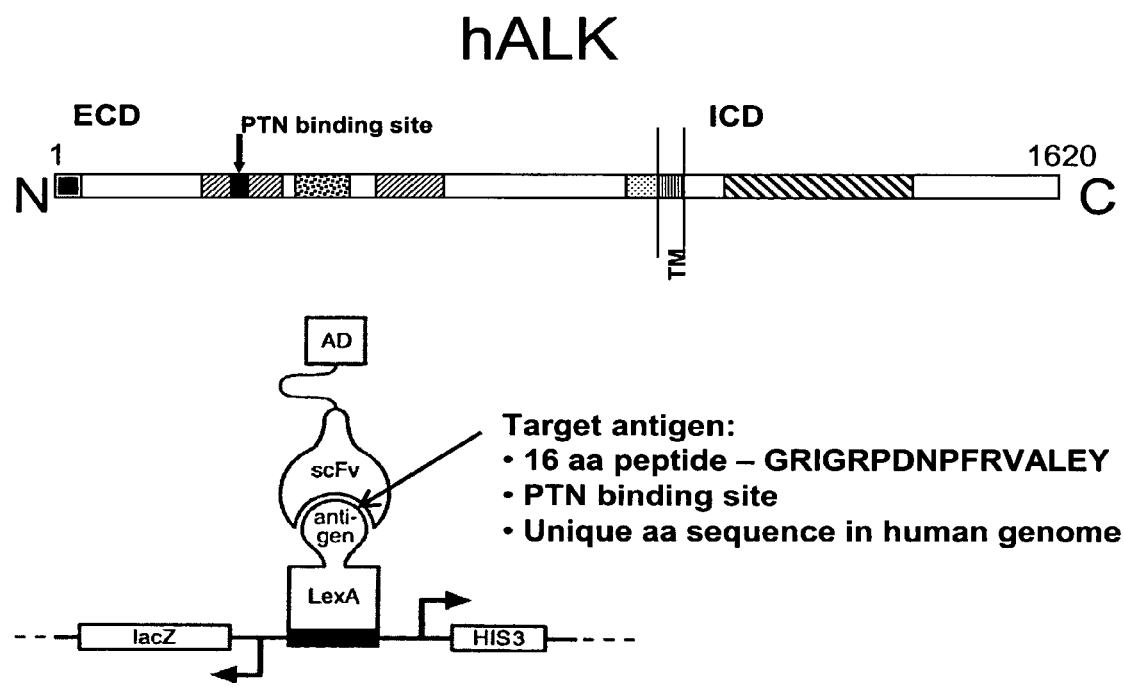
FIG. 1 shows a scheme of the human ALK protein used. A 16 amino acid peptide of the PTN binding site (dashed) is used as the epitope in a two hybrid screen for scFv binders.
Figure 2:
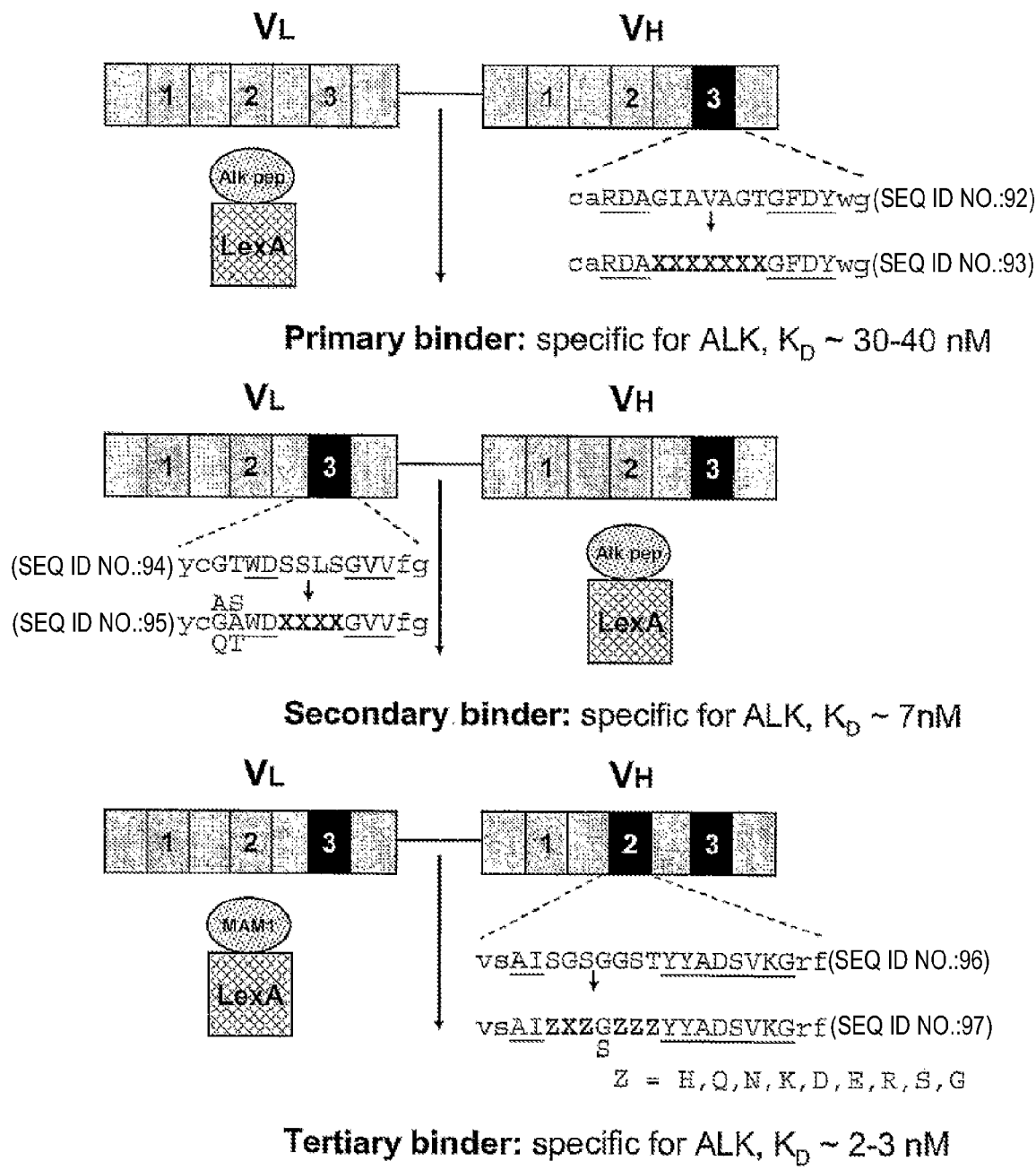
FIG. 2 shows the stepwise randomization of VH CDR3, VL CDR 3 and VH CDR 2 portions to obtain ESBA521 as secondary binder and a set of scFvs as tertiary binders (see Tab. 1). X stands for any amino acid residue.

In order that the present invention may be more readily understood, certain terms are first defined.

DEFINITIONS

The term "ALK" and "Alk-1" includes the human ALK protein encoded by the ALK (Anaplastic Lymphoma Kinase) gene which is a membrane-spanning protein tyrosine kinase (PTK)/receptor.

The term "antibody" refers to whole antibodies and any antigen binding fragment (i.e., "antigen-binding portion," "antigen binding polypeptide," or "immuno-binder") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refer to one or more fragments of an antibody that retain the ability to specifically bind to an antigen (e.g., ALK). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

The term "frameworks" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface. Such frameworks can also be referred to as scaffolds as they provide support for the presentation of the more divergent CDRs. Other CDRs and frameworks of the immunoglobulin superfamily, such as ankyrin repeats and fibronectin, can be used as antigen binding molecules (see also, for example, U.S. Pat. Nos. 6,300,064, 6,815,540 and U.S. Pub. No. 20040132028).

The term "epitope" or "antigenic determinant" refers to a site on an antigen to which an immunoglobulin or antibody specifically binds (e.g., ALK, for example, amino acid residues 391-406 of human ALK-1 (see e.g., SEQ ID NO: 1). An epitope typically includes at least 3, 4, 5, 6, 7, 8, 9, 10, 11, 12, 13, 14 or 15 amino acids in a unique spatial conformation. See, e.g., Epitope Mapping Protocols in Methods in Molecular Biology, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower.

The term "$K_D$," refers to the dissociation equilibrium constant of a particular antibody-antigen interaction. Typically, the antibodies of the invention bind to ALK with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The terms "neutralizes ALK," "inhibits ALK," and "blocks ALK" are used interchangeably to refer to the ability of an antibody of the invention to prevent ALK from interacting with one or more target ligands and, for example, triggering signal transduction.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand. Such hybridization conditions are know in the art, and described, e.g., in Sambrook et al. infra.

The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48): 444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The present invention also encompasses "conservative sequence modifications" of the sequences set forth in the SEQ ID NOs of the present invention, i.e., nucleotide and amino acid sequence modifications which do not abrogate the binding of the antibody encoded by the nucleotide sequence or containing the amino acid sequence, to the antigen. Such conservative sequence modifications include nucleotide and amino acid substitutions, additions and deletions. For example, modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-ALK antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

Alternatively, in another embodiment, mutations are randomly introduced along all or part of an anti-ALK antibody coding sequence, such as by saturation mutagenesis, and the resulting modified anti-ALK antibodies can be screened for binding activity. A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence.

By reference to the tables and figures provided herein a consensus sequence for the antibody heavy/light chain variable region CDR(s) can be derived by optimal alignment of the amino acid sequences of the variable region CDRs of the antibodies which are reactive against epitope 390-406 of the human ALK-1 protein.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which and expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

The terms "treat," "treating," and "treatment," refer to therapeutic or preventative measures described herein. The methods of "treatment" employ administration to a subject, in need of such treatment, an antibody of the present invention, for example, a subject having an ALK-mediated disorder or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "ALK-mediated disorder" refers to disease states and/or symptoms associated with ALK-mediated cancers or tumors. In general, the term "ALK-mediated disorder" refers to any disorder, the onset, progression or the persistence of the symptoms of which requires the participation of ALK. Exemplary ALK-mediated disorders include, but are not limited to, for example, cancer, in particular, glioblastoma.

The term "effective dose" or "effective dosage" refers to an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "subject" refers to any human or non-human animal. For example, the methods and compositions of the present invention can be used to treat a subject with a cancer, e.g., glioblastoma.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

The present invention provides in a first aspect an antibody binding the human ALK protein, said antibody comprising a variable heavy chain CDR3 of a sequence with at least 50% sequence identity to the sequence SEQ. ID. No. 2. Preferably, the sequence identity is at least 60%, 70%, 75%, 80%, or more preferably at least 90%. Most preferably, the CDR3 has the precise sequence of SEQ. ID. No. 2.

In a preferred embodiment of the present invention the antibody binds specifically to the human ALK protein, i.e., it does not bind to the mouse ALK protein, whose PTN binding site differs in only 2 amino acid residues compared to the PTN binding site (SEQ. ID. No. 1) of the human ALK protein. The human isoleucine at position 3 is a valine and the aspartate is an alanine in the corresponding mouse sequence.

The antibody of the present invention can be a full-length antibody, but also an antibody fragment, such as, for example, a scFv or a Fab fragment. Antigen binding fragments are well known in the art. Preferably, a scFv antibody is used.

The heavy chain and the light chain are composed of framework sequences, each comprising three CDRs, CDR1, CDR2 and CDR3, which are predominantly involved in antigen binding. The antibody of the present invention comprises the VH domain of the H3 type and a VL domain of the lambda1 type.

The VH and VL framework of the antibody of the present invention are stable and soluble so as to be functional in an intracellular reducing environment. Preferably it is the framework 4.4 that has previously been isolated by a yeast screening system referred to as the "Quality control system" (Auf der Maur et al., 2001; Auf der Maur et al. 2004). The sequence of the framework can be deduced for example from SEQ. ID. No. 20 (see below), where the framework portions are represented by non-underlined and straight letters, while the CDR sequences are underlined and the linker sequence is in italics.

The antibody of the present invention is able to bind a 16-amino acid ALK epitope peptide of a sequence that is at least 75%, preferably 80%, 85%, 90%, 95%, or most preferably 100%, identical to the sequence of SEQ. ID. No. 1. This sequence is also referred to as PTN binding site and is a unique sequence in the entire human genome. The corresponding mouse sequence varies in 2 out of 16 amino acids, i.e., V at position 3 and A at position 7 instead of I or D, respectively. Preferably, the antibody of the present invention binds human but not mouse ALK, i.e., is specific for the human protein. The ALK epitope comprising about residues 391-406 or consisting of these residues is uniquely suited for selecting an antibody or antigen binding fragment that can specifically bind ALK and block or inhibit ALK-mediated activity. This epitope is also suitable for screening or raising antibodies that specifically block ALK activity. Thus, this epitope, especially an epitope comprising about residues 391-406 or consisting of about these residues, is uniquely suited for use as an active immunotherapeutic agent or vaccine as further described herein.

The antibody of the present invention has an affinity for the ALK epitope peptide with a $K_d$ of 30 nM or less, preferably 10 nM or less, most preferably below 3 nM.

In another embodiment of the present invention, the antibody comprising a variable light chain CDR3 of a sequence with at least 50% sequence identity to the sequence SEQ. ID. No. 3. Preferably, the sequence identity is at least 60%, 70%, 80%, 85%, more preferably at least 90%. Most preferably, CDR3 is identical to SEQ. ID. No. 3. Again, this antibody binds a 16-amino-acid ALK epitope peptide of a sequence with at least 75%, preferably 80%, 85%, 90%, 95%, or most preferably 100%, amino acid identity to the sequence SEQ. ID. No. 1. Also, the antibody has an affinity for the ALK epitope peptide with a $K_d$ of less than 10 nM, preferably less than 7 nM.

In a preferred embodiment of the present invention the antibody comprises a VH sequence of SEQ. ID. No. 4 and a VL sequence of SEQ. ID. No. 5. Additionally, it can comprise at least one mutation in at least one of the CDRs resulting in a higher affinity characterized by a $K_d$ of less than about 3 nM. Said at least one mutation is preferably in CDR1 or CDR2 of VH and/or VL, most preferably in CDR2 of VH.

In another preferred embodiment of the present invention the antibody comprises a variable heavy chain CDR2 comprising a sequence selected from the group of SEQ. ID. No. 7, SEQ. ID. No. 8, SEQ. ID. No. 9, SEQ. ID. No. 10, SEQ. ID. No. 11, SEQ. ID. No. 12, or SEQ. ID. No. 13. Preferably these defined CDR2 sequences are preceded by the amino acids residues AI and followed by the sequences of SEQ. ID. No. 17, so that the entire CDR2 is defined.

A preferred antibody of the present invention comprises a VH sequence of SEQ. ID. No. 4 and a VL sequence of SEQ. ID. No. 5. In scFv antibodies, the domain structure can NH$_2$—VL-linker-VH—COOH or NH$_2$—VH-linker-VL-COOH; preferably, the linker has the sequence SEQ. ID. No. 16. Alternatively, the variable regions represented by SEQ ID NOS: 4 and 5 can be engineered into a full length antibody, e.g., IgG or IgM. Constant regions suitable for combining with the variable regions of the invention are known in the art.

Within the scope of the present invention is the use of the antibody or antibody derivative as a medicament or as a diagnostic tool. Preferably, the production of a medicament for the treatment of cancers or tumors is envisaged. For this purpose an antibody can be radiolabelled using radionuclides or radiometal labeling. This is particularly valuable for tumor targeting, imaging and biodistribution studies. Also, recombinant DNA technology makes it possible to genetically fuse coding regions of variable V genes to modified toxin domains. For example, a scFv-toxin fusion wherein the scFv is specific for a tumor marker protein can target the toxin to the tumor, where the toxin causes cytotoxicity. Such targeted therapy results in the selective concentration of cytotoxic agents or radionuclides in tumors and should lessen the toxicity to normal tissues.

In a preferred embodiment of the present invention the antibody is used for a treatment of cancers or tumors, preferably neuroblastoma, glioblastoma, rhabdomyosarcoma, breast carcinoma, melanoma, pancreatic cancer, B-cell non-Hodgkin's lymphoma, thyroid carcinoma, small cell lung carcinoma, retinoblastoma, Ewing sarcoma, prostate cancer, colon cancer, or pancreatic cancer, preferably glioblastoma, neuroblastoma and rhabdomyosarcoma. ALK expression and protein has been detected in many soft tissue tumors (Li et al., 2004). Full-length ALK has been found in these human tumors. Furthermore, the antibody is preferably used for local treatments. Most preferred is local treatment of glioblastoma.

Another aspect of the present invention is to provide a DNA sequence encoding the antibody of the present invention. A suitable prokaryotic expression vector for ESBA512 (SEQ. ID. No: 19) is pTFT74 (see SEQ. ID. No: 90 for the sequence including the ESBA512 coding sequence). Therein, the ESBA512 coding sequence is under the control of the T7-promoter and the recombinant gene product is usually purified over inclusion bodies. Another preferred prokaryotic expression vector is pAK400, wherein the ESBA512 sequence is his-tagged for simplified purification (see SEQ. ID. No: 89 for the sequence including the ESBA512 coding sequence). The gene product is secreted by the host cell into the periplasm.

In addition, an expression vector comprising said DNA sequence and a suitable host cell transformed with said expression vector is provided. Preferably, said host cell is an *E. coli* cell.

Yet another aspect of the present invention is the production of the antibody of the present invention, comprising culturing the host cell that is transformed with the expression vector for said antibody, under conditions that allow the synthesis of said antibody and recovering it from said culture.

Another aspect of the present invention is to provide an ALK epitope, comprising or consisting essentially of residues 391-406 of SEQ ID NO: 1. Said epitope is suitable for identifying, screening, or raising anti-ALK antibodies or fragments thereof. Preferably, the antibody or antigen binding fragment thereof that is capable of specifically binding residues 391-406 (SEQ ID NO:1) of an isolated ALK protein or fragment thereof. More preferably, the antibody is a single chain antibody (scFv), Fab fragment, IgG, or IgM.

In a further aspect, an ALK vaccine comprising an isolated ALK protein or a fragment thereof, or a nucleic acid encoding an epitope of ALK is provided. Preferably, the vaccine comprises residues 391-406 of an isolated ALK protein. Said vaccine is preferably formulated with a carrier, adjuvant, and/or hapten to enhance the immune response.

The sequences of the present invention are the following ones:

SEQ ID NO. 1:
GR<u>I</u>GRPDNPFRV<u>A</u>LEY

Human ALK epitope peptide (amino acids 391-406 of the ALK protein); underlined residues are different in the mouse homologue.

SEQ ID NO. 2:
RDA<u>WLD</u>V<u>L</u>SDGFDY

ESBA521 CDR 3 of VH. Residues obtained after randomization are underlined.

```
                    SEQ ID NO. 3:
                    ATWDNDKWGVV
```

ESBA521 CDR 3 of VL. Residues obtained after randomization are underlined.

```
SEQ ID NO. 4:
EVQLVESGGGLVQPGGSLRLSCAASGFTFSSYAMSWVRQAPGKGLEWVS

AISGSGGSTYYADSVKGRFTISRDNSKNTLYLQMNSLRAEDTAVYYCAR

DAWLDVLSDGFDYWGQGTLVTVSS
```

VH of ESBA521. CDRs are underlined.

```
SEQ ID NO. 5:
QSVLTQPPSVSAAPGQKVTISCSGSTSNIGDNYVSWYQQLPGTAPQLLI

YDNTKRPSGIPDRFSGSKSGTSATLGITGLQTGDEADYYCATWDNDKWG

VVFGGGTKLEVLG
```

VL of ESBA521. CDRs are underlined.

```
                    SEQ. ID. No. 6:
                    AISGSGGSTYYADSVKG
```

VH CDR 2 of ESBA521

```
                    SEQ ID NO. 7:
                    AINMKGNDRYYADSVGK
```

VH CDR 2 of scFv 265.1

```
                    SEQ ID NO. 8:
                    AIRTNSKEYYADSVKG
```

VH CDR 2 of scFv 43.2

```
   SEQ. ID. No. 9      AIKTDGNHKYYADSVKG
```

VH CDR 2 of scFv 100.2

```
                    SEQ ID NO. 10:
                    RTDSKEQYYADSVKG
```

VH CDR 2 of scFv 2.11

```
                    SEQ ID NO. 11:
                    ETSSGSTYYADSVKG
```

VH CDR 2 of scFv 28.11

```
                    SEQ ID NO. 12:
                    NTGGGSTYYADSVKG
```

VH CDR 2 of scFv 33.11

```
                    SEQ ID NO. 13:
                    NTRGQNEYYADSVKG
```

VH CDR 2 of scFv 4.12

```
   GGGGSGGGGSGGGGSSGGGS        SEQ ID NO. 16
```

Linker connecting VL and VH

```
   YYADSVKG            SEQ ID NO. 17
```

C-terminal half of CDR2 of ESBA521 and its derivatives.

```
   DAGIAVAGTGFDY            SEQ ID NO. 18
```

VH CDR3 of FW4.4

```
                                SEQ ID NO. 19
QSVLTQPPSVSAAPGQKVTISCSGSTSNIGDNYVSWYQQLPGTAPQLLIY

DNTKRPSGIPDRFSGSKSGTSATLGITGLQTGDEADYYCATWDNDKWGVV

FGGGTKLEVLGGGGGSGGGGSGGGGSSGGGSEVQLVESGGGLVQPGGSLR

LSCAASGFTFSSYAMSWVRQAPGKGLEWVSAISGSGGSTYYADSVKGRFT

ISRDNSKNTLYLQMNSLRAEDTAVYYCARDAWLDVLSDGFDYWGQGTLVT

VSS
``` scFv ESBA521, CDRs underlined, linker in italics

```
                                SEQ ID NO. 20
QSVLTQPPSVSAAPGQKVTISCSGSTSNIGDNYVSWYQQLPGTAPQLLIY

DNTKRPSGIPDRFSGSKSGTSATLGITGLQTGDEADYYCGTWDSSLSGVV

FGGGTKLTVLGGGGGSGGGGSGGGGSSGGGSEVQLVESGGGLVQPGGSLR

LSCAASGFTFSSYAMSWVRQAPGKGLEWVSAISGSGGSTYYADSVKGRFT

ISRDNSKNTLYLQMNSLRAEDTAVYYCARDAGIAVAGTGFDYWGQGTLVT

VSS
```

FW4.4, CDRs are underlined, linker in italics

```
                                SEQ ID NO. 21
cagtctgtgctgacgcagccgccctcagtgtctgcggccccagga cagaaggtcaccatctcctgctccggaagcacctccaacattggcgataa ttatgtatcctggtaccaacaactcccaggaacagccccccaactcctca tttatgacaatactaaacgaccctcagggattcctgaccggttctctggc tccaagtctggcacgtcagccaccctgggcatcaccggactccagactgg ggacgaggccgattattactgcgcgacctgggataatgataagtggggtg tggttttcggcggagggaccaagctcgaggtcc-taggt
```

Nucleic acid sequence of ESBA521 VL
CDRs are underlined

```
                                SEQ ID NO. 22
gaggtgcagctggtggagtccggggggaggcttggtacagcctggg gggtccctgagactctcctgtgcagcctctggattcacctttagcagcta tgccatgagctgggtccgccaggctccagggaaggggctggagtgggtct cagctattagtggtagtggtggtagcacatactacgcagactccgtgaag ggccggttcaccatctccagagacaattccaagaacacgctgtatctgca
```

-continued

```
aatgaacagcctgagagccgaggacacggccgtatattactgcgcgcgtg atgcgtggttggatgtgctttcggatggctttgactactggggccaggga accctggtcaccgtctcctcg
```

Nucleic acid sequence of ESBA521 VH
CDRs are underlined

SEQ ID NO. 23
```
cagtctgtgctgacgcagccgccctcagtgtctgcggcccagga cagaaggtcaccatctcctgctccggaagcacctccaacattggcgataa ttatgtatcctggtaccaacaactcccaggaacagcccccaactcctca tttatgacaatactaaacgaccctcagggattcctgaccggttctctggc tccaagtctggcacgtcagccaccctgggcatcaccggactccagactgg ggacgaggccgattattactgcgcgacctgggataatgataagtggggtg tggttttcggcggagggaccaagctcgaggtcctaggtggtggtggtggt tctggtggtggtggttctggcggcggcggctccagtggtggtggatccga ggtgcagctggtggagtccgggggaggcttggtacagcctggggggtccc tgagactctcctgtgcagcctctggattcaccttttagcagctatgccatg agctgggtccgccaggctccagggaaggggctggagtgggtctcagctat tagtggtagtggtggtagcacatactacgcagactccgtgaagggccggt tcaccatctccagagacaattccaagaacacgctgtatctgcaaatgaac agcctgagagccgaggacacggccgtatattactgcgcgcgtgatgcgtg gttggatgtgctttcggatggctttgactactggggccagggaaccctgg tcaccgtctcctcg
```

Nucleic acid sequence of ESBA521
CDRs are underlined, linker in italics

The invention is now further described by means of examples:

Materials and Methods

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning Cold Spring Harbor Laboratory Press* (1989); *Antibody Engineering Protocols (Methods in Molecular Biology)*, 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley & Sons (1992).

Experiment 1: Screening to Identify Alk-Binding scFvs

In a wealth of structural studies on antibody-antigen interactions it was found that residues in the complementarity-determining region 3 (CDR-H3) of the heavy chain generally contribute the most substantial contacts to the antigen (Chothia and Lesk, 1987; Chothia et al., 1985; Padlan, 1994). We applied our recently described yeast two-hybrid antigen-antibody interaction screening technology to directly isolate antigen-binding scFvs by screening of four scFv libraries of randomized synthetic CDR-H3 sequences (Auf der Maur et al., 2002). The four libraries are based on four different stable human scFv frameworks in which 7 amino acids within the third CDR loop of the variable heavy chain (VH-CDR3) were randomized. The randomized parts were introduced by standard PCR cloning techniques. The scFv libraries were screened against a 16 amino acid peptide derived from the extracellular domain of the human tyrosine receptor kinase Anaplastic Lymphoma Kinase (ALK) by a yeast screening system called "Quality Control" (Auf der Maur et al., 2001; Auf der Maur et al., 2004). Briefly, the Quality Control technology is an antigen-independent intrabody selection system for identifying from a natural pool of human variable-light (VL) and variable-heavy (VH) chains those VL and VH combinations with favourable biophysical properties, such as stability, solubility and expression yield. One promising and specific binder from one of the four scFv libraries was isolated after the first screening round. This particular scFv was derived from the framework FW4.4 library. FW4.4 (SEQ. ID. No. 20) consists of a VL domain (lambda1) connected by a classical flexible glycine-serine linker (GGGGS).sub.4 to a VH.sub.3 domain. The VH CDR3 of FW4.4 comprises 13 amino acids (DAGIAVAGTGFDY; SEQ. ID. No. 18). To construct the library, the central part of the VH CDR3 (DAXXXXXXXGFDY) (SEQ ID NO: 98) was randomized by standard PCR-cloning methods using a degenerated oligonucleotide. The last two residues (Asp and Tyr) were kept constant, because their structural importance was demonstrated in many cases (Chothia and Lesk, 1987). The remaining residues were not modified in order to keep the complexity of the library in manageable dimensions. The scFv library was cloned in a yeast expression vector (pLib1) as C-terminal fusion to the transcriptional activation domain of Gal4 (Auf der Maur et al., 2002).

The ligand-binding domain (LBD) of human Alk was chosen as antigen for the interaction screen (Stoica et al., 2001). This 16 amino acid peptide was cloned into another yeast expression vector (pBait1) as C-terminal fusion to the DNA-binding protein LexA.

The reporter yeast strain YDE173 (Auf der Maur et al., 2002) containing the stably integrated reporter genes HIS3 and lacZ under the control of six LexA-binding sites was transformed with the bait vector expressing the Alk LBD fused to LexA together with the random CDR-H3 scFv library fused to the Gal4 activation domain. Transformed cells were selected on plates lacking histidine and containing 2.5 mM 3-amino-triazole (3-AT), which is a competitive inhibitor of the HIS3 gene product. Growing colonies were picked over a period of six days and the library plasmids were isolated. The same reporter strain was transformed with the rescued plasmids to confirm antigen-dependent gene activation. A quantitative liquid β-galactosidase assay was performed to measure binding-strength between the Alk LBD, i.e. the 16 amino acid ALK peptide, and the selected scFv. The scFv with highest reporter gene activation also demonstrated best affinity (~31 nM) for the Alk LBD peptide in ELISA (data not shown).

The sequences of other VH CDR3 sequences identified as contributing to ALK binding are provided below in Table 1a.

| clone | VH CDR 3 (mutated residues) | |
|---|---|---|
| WT FW4.4 | DAGIAVAGTGFDY | (SEQ ID NO. 24) |
| H5 SH 2.1 | DAKFMSDGIGFDY | (SEQ ID NO. 25) |
| H5 SH 4.1 | DAWGWTILSGFDY | (SEQ ID NO. 26) |

| clone | VH CDR 3 (mutated residues) | |
|---|---|---|
| H5 SH 5.1 | DAAYMIRYEGFDY | (SEQ ID NO. 27) |
| H5 SH 2.3 | DAWIYWAREGFDY | (SEQ ID NO. 28) |
| H5 SH 3.3 | DACMTYSREGFDY | (SEQ ID NO. 29) |
| H5 SH 5.3 | DAWLDVLSDGFDY | (SEQ ID NO. 30) |
| H5 SH 14.3 | DAPSVNDREGFDY | (SEQ ID NO. 31) |

The sequences of other suitable frameworks are provided below in Table 1b.

| FW | Sequence |
|---|---|
| 5.2 | EIVLTQSPATLSLSPGERATLSCRASQTLTHYLAWYQQKPGQAPRL LIYDTSKRATGTPARFSGSGSGTDFTLTISSLEPEDSALYYCQQRN SWPHTFGGGTKLEIKRGGGGSGGGGSGGGGSSGGGSEVQLVESGG GVAQPGGSLRVSCAASGFSFSSYAMQWVRQAPGKGLEWVAVISNDG RIEHYADAVRGRFTISRDNSQNTVFLQMNSLRSDDTALYYCAREIG ATGYLDNWGQGTLVTVSS (SEQ ID NO. 15) |

Experiment 2: Affinity Maturation

In order to obtain an scFv with higher affinity, this primary binder was subjected to a further affinity maturation process by mutagenesis and a second screening round in yeast. Enabling affinity maturation, the expression level of the LexA Alk LBD peptide fusion protein was reduced in order to lessen reporter gene activation driven by the interaction of the primary binder with the Alk LBD peptide. The strong actin promoter on the pBait1 vector was exchanged with the truncated and thus less active version of the ADH promoter (alcohol dehydrogenase) resulting in pBait3. This reduction of the bait expression level, in the presence of the primary binder, was sufficient to inhibit growth on plates lacking histidine and containing 5 mM 3-AT. Mutagenesis of the primary binder for affinity maturation was accomplished by randomizing parts of the CDR3 within the variable light chain. This was performed directly in yeast by homologous recombination (Schaerer-Brodbeck and Barberis, 2004). The VL CDR3 of FW4.4 comprises 11 amino acids (SEQ. ID. No. 14: GTWDSSLSGVV). The first two positions were partially randomized, such that the first position either encodes Gly, Ala or Gln, and the second position Thr, Ser or Ala. At the positions 5 to 8 within VL CDR3 all amino acid residues were allowed. The remaining positions were kept constant. Randomization was introduced by PCR. The resulting PCR product had a size of 356 bp and comprised the randomized CDR cassette with 267 bp upstream and 27 bp downstream framework sequences. This product is the so-called donor PCR fragment, which bears homologies to the target vector. The target vector is the yeast plasmid (pLib1) encoding the primary binder fused to the activation domain of Gal4. In order to improve efficiency of homologous recombination and to exclude false positives in the subsequent screening, the CDR-L3 in the target vector was slightly modified. A unique SacI restriction site was introduced in the middle of VL CDR3, which leads to a frameshift in the scFv encoding part of the fusion protein and results in a truncated protein unable to bind to the Alk LBD. In addition, the SacI site enables linearization of the target vector, which enhances recombination efficiency in yeast.

The screening was launched by pre-transformation of the reporter yeast strain YDE173 with the plasmid (pBait3) expressing the LexA Alk LBD from the truncated ADH promoter. This pre-transformed yeast cells were made competent again and co-transformed with the linearized target vector and with the donor PCR fragment, which bears homologies upstream and downstream of the VL CDR3. Upon homologous recombination between the PCR product and the target vector, the novel VL CDR3 sequence is integrated into the corresponding site of the target vector. As a net result of this event the primordial VL CDR3 gets exchanged with the randomized VL CDR3. This allows reconstitution of a circular plasmid that expresses a fully functional fusion protein with a novel VL CDR3 sequence, which will activate reporter gene expression and enable growth on selective plates upon interaction with the Alk LBD peptide.

Figure 3:
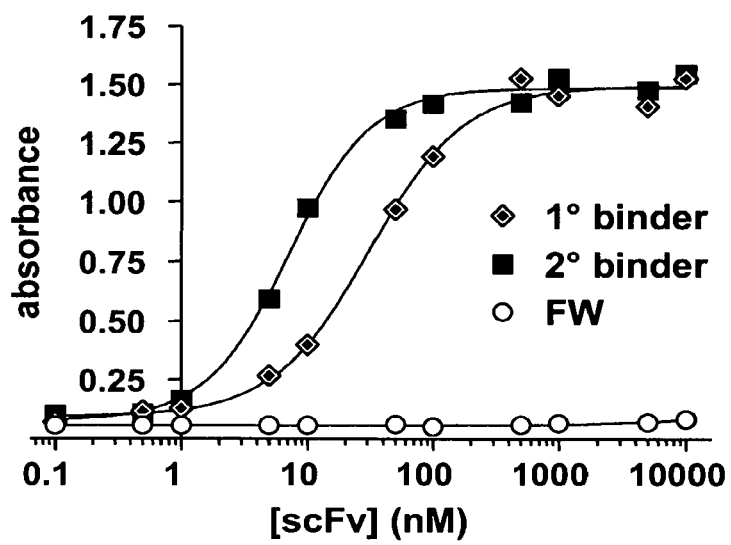

A total of 119 clones grew on selective plates over an observation period of 6 days. These clones were picked and the library plasmids were isolated and retransformed into the same reporter yeast strain. A quantitative liquid β-galactosidase assay was performed to measure binding strength between the Alk LBD (antigen) and the affinity-matured scFv. 20 clones with highest lacZ activation were also tested in ELISA with Alk LBD peptide. The best candidate revealed a $K_D$ of about 7 nM (FIG. 3) and was named ESBA521.

The sequences of other VL CDR3 sequences identified as contributing to ALK binding are provided below in Table 1c.

| clone | VL CDR 3 | |
|---|---|---|
| WT FW4.4 | GTWDSSLSGVV | (SEQ ID NO. 32) |
| 5.3-9.1 | AAWDSVKHGVV | (SEQ ID NO. 33) |
| 5.3-21.1 | AAWDNSMRGVV | (SEQ ID NO. 34) |
| 5.3-22.1 | AAWDTMRYGVV | (SEQ ID NO. 35) |
| 5.3-25.1 | AAWDTTRVGVV | (SEQ ID NO. 36) |
| 5.3-27.1 | ASWDTMLKGVV | (SEQ ID NO. 37) |
| 5.3-28.1 | ASWDTPTCGVV | (SEQ ID NO. 38) |
| 5.3-29.1 | ATWDISRCGVV | (SEQ ID NO. 39) |
| 5.3-46.1 | ATWDTVCAGVV | (SEQ ID NO. 40) |
| 5.3-53.1 | ATWDVDVFGVV | (SEQ ID NO. 41) |
| 5.3-57.1 | ATWDDVVGGVV | (SEQ ID NO. 42) |
| 5.3-86.1 | AAWDSFYNGVV | (SEQ ID NO. 43) |
| 5.3-94.1 | ASWDTLIEGVV | (SEQ ID NO. 44) |
| 5.3-107.1 | ATWDNDKWGVV | (SEQ ID NO. 45) |
| 5.3-112.1 | AAWDSTTCGVV | (SEQ ID NO. 46) |
| 5.3-113.1 | ATWDMWMKGVV | (SEQ ID NO. 47) |
| 5.3-117.1 | GTWDSSLSGVV | (SEQ ID NO. 48) |
| 5.3-118.1 | AAWDWVLGGVV | (SEQ ID NO. 49) |
| 14.3-6.1 | ATWDNPGQGVV | (SEQ ID NO. 50) |
| 14.3-7.1 | ATWDDWVIGVV | (SEQ ID NO. 51) |

| clone | VL CDR 3 | |
|---|---|---|
| 14.3-8.1 | ASWDDQKWGVV | (SEQ ID NO. 52) |
| 14.3-9.1 | ATWDTNRHGVV | (SEQ ID NO. 53) |
| 14.3-12.1 | ASWDDLHIGVV | (SEQ ID NO. 54) |
| 14.3-13.1 | ASWDEEAWGVV | (SEQ ID NO. 55) |
| 14.3-21.1 | ATWDYIKIGVV | (SEQ ID NO. 56) |
| 14.3-48.1 | ATWDTFERGVV | (SEQ ID NO. 57) |
| 14.3-49.1 | ATWDSNLIGVV | (SEQ ID NO. 58) |
| 5.3-24., 1 | ATWDNNTCGVV | (SEQ ID NO. 59) |
| 5.3-3.1 | AAWDCDINGVV | (SEQ ID NO. 60) |
| 5.3-8.1 | ASWDSMKIGVV | (SEQ ID NO. 61) |
| 5.3-19.1 | ATWDCTRAGVV | (SEQ ID NO. 62) |

Figure 4:
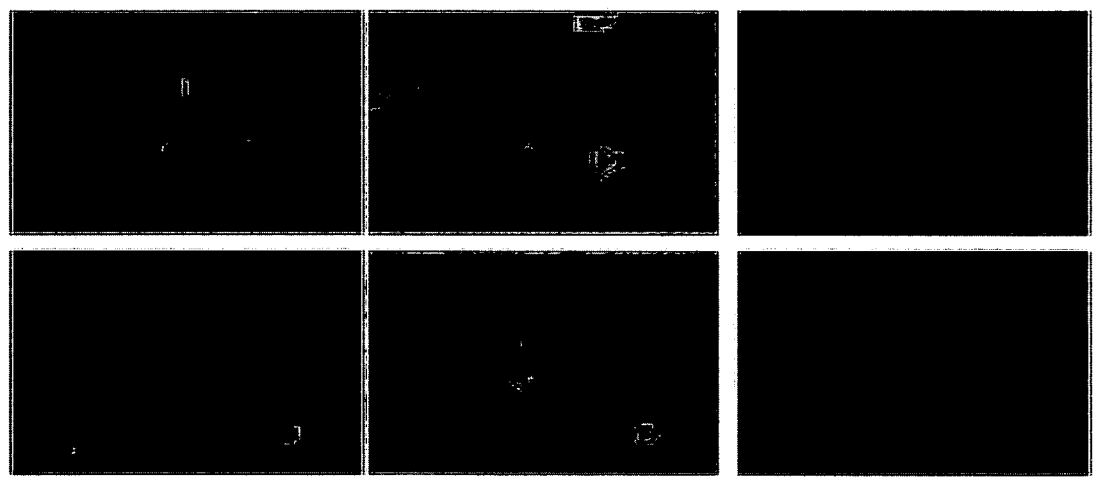
FIG. 4 shows immunostaining of transiently transfected HeLa cells with ESBA521 (left panels) and a polyclonal ALK specific antibody (right panels). Middle panel: same cells visualized by light microscopy.

Experiment 3: The scFv ESBA521 Specifically Binds to the Transmembrane Form of Human ALK In order to test whether the newly identified scFv was able to also recognize the transmembrane human ALK protein on the surface of living cells, immunostaining experiments of transiently transfected HELA cells were performed. ESBA521 reacts with the ALK protein in a comparable way as a polyclonal antibody (FIG. 4). In a control experiment it was shown that the framework 4.4 scFv does not react with human ALK. Surprisingly, ESBA521 only binds to the human Alk protein, but not to the corresponding mouse protein, although the mouse antigenic peptide only differs in two amino acid positions from the human peptide sequence. By contrast, the polyclonal ALK antibody recognizes both human and mouse protein. Therefore, binding of ESBA521 is specific for the human ALK protein at the cell surface.

Experiment 4: Isolation of Improved Binders by PCR Mutagenesis of VH CDR 2

To further improve antigen binding, ESBA521 was used as the starting scFv in a further round of affinity maturation using the same two-hybrid approach as described for the first round of affinity maturation, except in this case CDR2 of VH was changed by PCR mutagenesis and transformed into the yeast recipient, wherein homologous recombination at CDR2 is enforced in analogous way. Again, a restriction site was introduced in CDR2 to enable linearization of the target plasmid. The mutations introduced in CDR2 are given in Table 2.

| scFv (performing best) | VH CDR 2 (mutated residues) | |
|---|---|---|
| WT (ESBA521) | AISGSGGSTYYADSVKG | (SEQ ID NO. 63) |
| 1.1 | AI-KTDGQNYYADSVKG | (SEQ ID NO. 64) |
| 17.1 | AIRSDGNERYYADSVKG | (SEQ ID NO. 65) |
| 35.1 | AINTNGNEKYYADSVKG | (SEQ ID NO. 66) |
| 64.1 | AISTNGKERYYADSVKG | (SEQ ID NO. 67) |
| 130.1 | AIRTQSQEEYYADSVKG | (SEQ ID NO. 68) |
| 152.1 | AIKSRSQEQYYADSVKG | (SEQ ID NO. 69) |

| scFv (performing best) | VH CDR 2 (mutated residues) | |
|---|---|---|
| 167.1 | AIKSHSQQQYYADSVKG | (SEQ ID NO. 70) |
| 214.1 | AINSEGQQRYYADSVKG | (SEQ ID NO. 71) |
| 225.1 | AIKSKGQNKYYADSVKG | (SEQ ID NO. 72) |
| 262.1 | AIRTNSEEKYYADSVKG | (SEQ ID NO. 73) |
| 265.1 | AINMKGNDRYYADSVKG | (SEQ ID NO. 74) |
| 43.2 | AI-RTNSKEYYADSVKG | (SEQ ID NO. 75) |
| 70.2 | AIKTESQQRYYADSVKG | (SEQ ID NO. 76) |
| 99.2 | AINSNGKQDYYADSVKG | (SEQ ID NO. 77) |
| 100.2 | AIKTDGNHKYYADSVKG | (SEQ ID NO. 78) |
| 109.2 | AIDTKGNGQYYADSVKG | (SEQ ID NO. 79) |
| 146.2 | AIRSDSSHKYYADSVKG | (SEQ ID NO. 80) |
| 173.2 | AINTKSNEQYYADSVKG | (SEQ ID NO. 81) |
| 199.2 | AIRTDSKNSYYADSVKG | (SEQ ID NO. 82) |
| 2.11 | AIRTDSKEQYYADSVKG | (SEQ ID NO. 83) |
| 19.11 | AIRTNSKEEYYADSVKG | (SEQ ID NO. 84) |
| 28.11 | AIETSSGSTYYADSVKG | (SEQ ID NO. 85) |
| 33.11 | AINTGGGSTYYADSVKG | (SEQ ID NO. 86) |
| 4.12 | AINTRGQNEYYADSVKG | (SEQ ID NO. 87) |
| 6.12 | AISTSG-STYYADSVKG | (SEQ ID NO. 88) |

Figure 5:
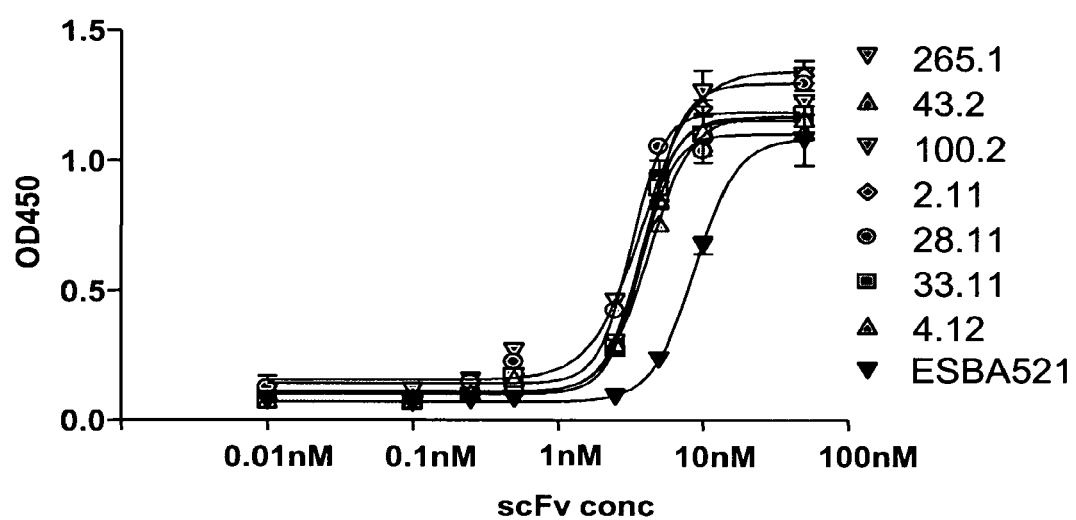
FIG. 5 shows an ELISA experiment comparing the ESBA512 to the improved tertiary binders.

Among the isolated scFvs obtained after this procedure, seven turned out to have significantly improved affinity with a $K_d$ in the range of 2-3 nM (FIG. 5), the best of them being 28.11.

Experiment 5: Prevention of Tumor-Growth Upon Administration of Anti-ALK Antibody The progenitors of the antibody ESBA521 were selected to bind to amino acids 391-406 of ALK, which comprises the amino acids (396-406) that are known to bind pleiotrophin (Stoica 2001). ESBA521 was obtained by randomizing additional amino acids in the CDRs of its progenitor and by selecting for binders that bind to the 391-406 amino acid stretch contained in its natural context of the ALK extracellular domain (ECD). These proceedings resulted in an antibody, which binds the ALK ECD with high affinity at the same site that binds PTN. To our knowledge. This is the first monoclonal antibody that specifically targets the PTN binding site of ALK. Accordingly, ESBA521 is predicted to have high affinity to the ALK ECD and efficiently competes with pleiotrophin (PTN) and midkine (MK) for binding to the ALK receptor, and thus, the ESBA521 antibody is suitable for inhibiting both MK and PTN ligand binding to the ALK protein.

Because ALK and its ligands are involved in neoplasia, tumor invasion and angiogenesis, inhibition of the interaction between ALK and its cognate ligands disrupts ALK mediated tumorgenesis.

The effect of ESBA521 on a specific tumor can be determined by the following two assays described below.

In a first assay, xenograft experiments are prepared in order to determine the cancer growth rate-limiting role of ALK (Powers 2002). Briefly, a U87MG cell suspension of 20 million cells/ml media supplemented with 10% fetal calf serum are prepared. These are injected into NU/NU mice and resultant tumors are measured. Test antibodies, preferably full length antibodies, more preferably, pegylated antibodies, are introduced and tumor growth is assessed.

While there are shown and described presently preferred embodiments of the invention, it is to be distinctly understood that the invention is not limited thereto but may be otherwise variously embodied and practiced within the scope of the following claims.

REFERENCES

Auf der Maur, A., Escher, D., and Barberis, A. (2001). Antigen-independent selection of stable intracellular single-chain antibodies. FEBS Lett 508, 407-412.

Auf der Maur, A., Tissot, K., and Barberis, A. (2004). Antigen-independent selection of intracellular stable antibody frameworks. Methods 34, 215-224.

Auf der Maur, A., et al., Direct in vivo screening of intrabody libraries constructed on a highly stable single-chain framework. J Biol Chem, 277(47): p. 45075-85, 2002.

Bai R Y. et al. Nucleophosmin-anaplastic lymphoma kinase associated with anaplastic large-cell lymphoma activates the phosphatidylinositol 3-kinase/Akt anti-apoptotic signalling pathway. Blood 96(13), 4319-4327, 2000.

Bowden et al. Anti-apoptotic signaling of pleiotrophin through its receptor, anaplastic lymphoma kinase. The Journal of Biological Chemistry 277(39), 35862-35868, 2002.

Chothia, C., and Lesk, A. M. (1987). Canonical structures for the hypervariable regions of immunoglobulins. J. Mol. Biol. 196, 901-917.

Chothia, C., Novotny, J., Bruccoleri, R., and Karplus, M. (1985). Domain association in immunoglobulin molecules. The packing of variable domains. J. Mol. Biol. 186, 651-663.

Choudhuri et al., An Angiogenic Role for the Neurokines Midkine and Pleiotrophin in Tumorigenesis. Cancer Res. 57, 1814-1819, 1997.

Czubayko et al., Melanoma angiogenesis and metastasis modulated by ribozyme targeting of the secreted growth factor pleiotrophin. PNAS 93, 14753-14758, 1996.

De Juan C. et al. Genomic organization of a novel glycosylphosphatidylinositol MAM gene expressed in human tissues and tumors. Oncogene 21, 3089-3094, 2002.

Delsol G. et al. A new subtype of large B-cell lymphoma expressing the ALK kinase and lacking the 2;5 translocation. Blood 89(5), 1483-1490, 1997.

Dirks W G. et al. Expression and functional analysis of the anaplastic lymphoma kinase (ALK) gene in tumor cell lines. International Journal of cancer 100, 49-56, 2002.

Duyster J. et al. Translocations involving anaplastic lymphoma kinase (ALK). Oncogene 20, 5623-5637, 2001.

Ergin M. et al. Inhibition of tyrosine kinase activity induces caspase-dependent apoptosis in anaplastic large cell lymphoma with NPM-ALK (p80) fusion protein. Experimental Hematology 29, 1082-1090, 2001.

Fang et al., Pleiotrophin stimulates fibroblasts and endothelial and epithelial cells and is expressed in human cancer. JBC vol. 267 p. 25889, 1992.

Fiorani C. et al. Primary systemic anaplastic large-cell lymphoma (CD30+): advances in biology and current therapeutic approaches. Clinical Lymphoma 2(1), 29-37, 2001.

Iwahara T. et al. Molecular characterization of ALK, a receptor tyrosine kinase expressed specifically in the nervous system. Oncogene 14, 439-449, 1997.

Kutok J L. and Aster J C. Molecular biology of anaplastic lymphoma kinase-positive anaplastic large-cell lymphoma. Journal of Clinical Oncology 20(17), 3691-3702, 2002.

Ladanyi M. Aberrant ALK tyrosine kinase signalling. Different cellular lineages, common oncogenic mechanisms? American Journal of Pathology 157(2), 341-345, 2000.

Lamant et al. Expression of the ALK tyrosine kinase gene in neuroblastoma. Am. J. Pathol. 156, 1711-1721, 2000.

Li, X.-Q., Hisaoka, M., Shi, D.-R., Zhu, X-Z., and Hashimoto, H. Expression of Anaplastic Lymphoma Kinase in soft tissue tumors: an immunohistochemical and molecular study of 249 cases. Human pathology 35, 711-721, 2004.

Loren C E. et al. Identification and characterization of Dalk: a novel *Drosophila melanogaster* RTK which drives ERK activation in vivo. Genes to cells 6(6), 531-544, 2001.

Miyake I. et al. Activation of anaplastic lymphoma kinase is responsible for hyperphosphorylation of ShcC in neuroblastoma cell lines. Oncogene 21, 5823-5834, 2002.

Morris S W. et al. ALK, the chromosome 2 gene locus altered by the t(2;5) in non-Hodgkin's lymphoma, encodes a novel neural receptor tyrosine kinase that is highly related to leukocyte tyrosine kinase (LTK). Oncogene 14, 2175-2188, 1997.

Morris S W. et al. ALK+CD30+ lymphomas: A distinct molecular genetic subtype of non-Hodgkin's lymphoma. British Journal of Haematology 113, 275-295, 2001.

O'Brien et al., The angiogenic factor midkine is expressed in bladder cancer and overexpression correlates with a poor outcome in patients with invasive cancer. Cancer Res. 56, 2515-2518, 1996.

Padlan, E. A, (1994). Anatomy of the antibody molecule. Mol Immunol 31, 169-217.

Powers C. et al. Pleiotrophin signalling through anaplastic lymphoma kinase is rate-limiting for glioblastoma growth. The Journal of biological chemistry 277(16), 14153-14158, 2002.

Pulford K. et al. Anaplastic lymphoma kinase proteins and malignancy. Current Opinion in Hematology 81, 231-236, 2001.

Pulford K. et al. Anaplastic lymphoma kinase proteins in growth control and cancer. J Cell Physiol 199, 330-358, 2004.

Schaerer-Brodbeck, C. and A. Barberis, Coupling homologous recombination with growth selection in yeast: a tool for construction of random DNA sequence libraries. Biotechniques, 37(2): p. 202-206, 2004.

Stoica G E. et al. Identification of anaplastic lymphoma kinase as a receptor for the growth factor pleiotrophin. The Journal of Biological Chemistry 276(20), 16772-16779, 2001.

Stoica G E. et al. Midkine binds to anaplastic lymphoma kinase (ALK) and acts as a growth factor for different cell types. The Journal of Biological Chemistry 277 (39), 35990-35998, 2002.

Weber D. et al. Pleiotrophin can be rate-limiting for pancreatic cancer cell growth. Cancer Research 60, 5284-5288, 2000.

Wellstein et al., A Heparin-binding Growth Factor Secreted from Breast Cancer Cells Homologous to a Developmentally Regulated Cytokine. JBC Vol 267, p 2582, 1992.

SWISSPROT: www.expasy.org
www.emedicine.com/med/topic2692.htm (glioblastoma)
www.emedicine.com/MED/topic3205.htm (ALCL)

The invention claimed is:

1. A method for the treatment of glioblastoma in a subject suffering therefrom comprising administering to the subject a monoclonal antibody or antigen binding fragment thereof, wherein said antibody or fragment specifically binds human ALK protein, said antibody comprising a heavy chain variable region (VH) domain and a light chain variable region (VL) domain, said heavy chain variable region domain comprising the 3 CDRs in SEQ ID NO: 4 and said light chain variable region domain comprising the 3 CDRs in SEQ ID NO:5, thereby treating glioblastoma in the subject.

2. A method for the treatment of glioblastoma in a subject suffering therefrom, comprising administering to the subject an monoclonal antibody or antigen binding fragment thereof, wherein said antibody or fragment specifically binds human ALK protein, said antibody comprising a heavy chain variable region domain comprising the sequence of SEQ ID NO:4 and a light chain variable region domain comprising the sequence of SEQ ID NO:5, thereby treating glioblastoma in the subject.

3. The method of claim 1, wherein the antibody is administered in combination with an anticancer agent.

4. The method of claim 3, wherein the anticancer agent is methotrexate.

5. The method of claim 1, wherein the monoclonal antibody or fragment is selected from the group consisting of a single chain antibody (scFv), a Fab fragment, an IgG antibody and an IgM antibody.

6. The method of claim 1, said antibody or fragment having a binding affinity for the ALK epitope characterized by a $K_d$ of 30 nM or less.

7. The method of claim 1, said antibody or fragment having a binding affinity for the ALK epitope characterized by a $K_d$ of less than 3 nM.

8. The method of claim 1, wherein the VH and VL domains comprise frameworks that are stable and soluble so as to be functional in an intracellular reducing environment.

9. The method of claim 1, wherein the antibody or fragment thereof is derived from framework 4.4 (SEQ ID NO: 20).

10. The method of claim 1, wherein the VH domain is a H3 VH domain and the VL domain is a lambda1 VL domain.

11. The method of claim 2, wherein the antibody is administered in combination with an anticancer agent.

12. The method of claim 11, wherein the anticancer agent is methotrexate.

13. The method of claim 2, wherein the monoclonal antibody or fragment is selected from the group consisting of a single chain antibody (scFv), a Fab fragment, an IgG antibody and an IgM antibody.

14. The method of claim 2, said antibody or fragment having a binding affinity for the ALK epitope characterized by a $K_d$ of 30 nM or less.

15. The method of claim 2, said antibody or fragment having a binding affinity for the ALK epitope characterized by a $K_d$ of less than 3 nM.

16. The method of claim 2, said antibody comprising the structure $NH_2$-VL-linker-VH—COOH or $NH_2$-

VH-linker-VL-COOH, wherein the linker has the sequence GGGGSGGGGSGGGGSSGGGS (SEQ ID NO: 16).

* * * * *